United States Patent
Batey et al.

(10) Patent No.: US 12,416,008 B2
(45) Date of Patent: Sep. 16, 2025

(54) COMPOSITIONS AND METHODS OF USE FOR SMALL-MOLECULE REGULATION OF CRISPR-CAS9 ACTIVITY USING RNA APTAMERS

(71) Applicants: THE REGENTS OF THE UNIVERSITY OF COLORADO, A BODY CORPORATE, Denver, CO (US); INSCRIPTA INC., Boulder, CO (US)

(72) Inventors: Robert Batey, Boulder, CO (US); Roman S. Iwasaki Cordero, Boulder, CO (US); Andrew Garst, Boulder, CO (US)

(73) Assignees: The Regents of the University of Colorado, a body corporate, Denver, CO (US); Inscripta Inc., Boulder, CO (US)

( * ) Notice: Subject to any disclaimer, the term of this patent is extended or adjusted under 35 U.S.C. 154(b) by 910 days.

(21) Appl. No.: 17/375,808

(22) Filed: Jul. 14, 2021

(65) Prior Publication Data
US 2022/0042019 A1 Feb. 10, 2022

Related U.S. Application Data

(63) Continuation of application No. PCT/US2020/013718, filed on Jan. 15, 2020.

(60) Provisional application No. 62/793,748, filed on Jan. 17, 2019.

(51) Int. Cl.
*C12N 15/115* (2010.01)
*C12N 9/22* (2006.01)
*C12N 15/11* (2006.01)

(52) U.S. Cl.
CPC .............. *C12N 15/115* (2013.01); *C12N 9/22* (2013.01); *C12N 15/111* (2013.01); *C12N 2310/16* (2013.01); *C12N 2310/20* (2017.05)

(58) Field of Classification Search
CPC ........ C12N 15/115; C12N 9/22; C12N 15/111
See application file for complete search history.

(56) References Cited

U.S. PATENT DOCUMENTS

2007/0077571 A1 4/2007 Ellington et al.
2018/0119120 A1 5/2018 Donohoue et al.

FOREIGN PATENT DOCUMENTS

| CN | 107245493 A | 10/2017 |
| WO | 2015/035139 A2 | 3/2015 |
| WO | 2019/005856 A1 | 1/2019 |

OTHER PUBLICATIONS

Behlke et al., Genetic Engineering and Biotechnology News (2016) 36(5), retrieved from the internet: https://www.genengnews.com/resources/cleaning-up-crispr/ (Year: 2016).*
Tang et al., Nature Communications (2017) 8: 1-8 (Year: 2017).*
Nowak, et al., Nucleic Acids Research (2016) 44(20): 9555-9564 (Year: 2016).*
Briner et al., Molecular Cell (2014) 56: 33-339 (Year: 2014).*
McKeague, et al., Journal of nucleic Acids (2012) 2012: 1-20 (Year: 2012).*
Kundert Kale et al. Controlling CRISPR-Cas9 with ligand-activated and ligand-deactivated sgRNAs. BioRxiv, May 15, 2018, 56 pgs.
Ma Hanhui et al. CRISPR-Sirius: RNA scaffolds for signal amplification in genome imaging. Nature Methods, vol. 15, Nov. 2018, pp. 928-931.
Chen Hao et al. Aptazyme-mediated direct modulation of post-transcriptional sgRNA level for conditional genome editing and gene expression. Journal of Biotechnology, vol. 288, Nov. 1, 2018, pp. 23-29.
Weixin Tang et al. Aptazyme-embedded guide RNAs enable ligand-responsive genome editing and transcriptional activation. Nature Communications, vol. 8, Jun. 28, 2017, p. 15939.
Yuchen Liu et al. Directing cellular information flow via CRISPR signal conductors. Nature Methods, vol. 13, No. 11, Sep. 5, 2016, pp. 938-944.
Quentin R. V. Ferry et al. Rational design of inducible CRISPR guide RNAs for de novo assembly of transcriptional programs. Nature Communications, vol. 8, Mar. 3, 2017, p. 14633.
Lee Sang Won et al. Ultrafast Dynamics Show that the Theophylline and 3-Methylxanthine Aptamers Employ a Conformational Capture Mechanism for Binding Their Ligands. Biochemistry, vol. 49, No. 13, Mar. 9, 2010, pp. 2943-2951.
Kundert Kale et al. Controlling CRISPR-Cas9 with ligand-activated and ligand-deactivated sg RNAs. Nature Communications, vol. 10, No. 1, May 9, 2019.
Iwasaki Roman S. et al. Small molecule regulated sgRNAs enable control of genome editing in *E. coli* by Cas9. Nature Communications, vol. 11, No. 1, Mar. 13, 2020.

* cited by examiner

*Primary Examiner* — Evelyn Y Pyla
*Assistant Examiner* — Katherine R Small
(74) *Attorney, Agent, or Firm* — Polsinelli PC

(57) ABSTRACT

Provided herein are single guide RNAs (sgRNAs) that comprise aptamer sequences and related compositions and methods. Also provided herein are methods of selecting inducible sgRNAs that comprise aptamer sequences.

19 Claims, 14 Drawing Sheets
Specification includes a Sequence Listing.

SEQUENCE LISTING

```
<160> NUMBER OF SEQ ID NOS: 188

<210> SEQ ID NO 1
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 1
agagctagca agtt                                                        14

<210> SEQ ID NO 2
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 2
gtatcgctta agcc                                                        14

<210> SEQ ID NO 3
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 3
agtgagctaa aaat                                                        14

<210> SEQ ID NO 4
<211> LENGTH: 14
<212> TYPE: DNA
<213> ORGANISM: Artificial Sequence
<220> FEATURE:
<223> OTHER INFORMATION: Synthetic polynucleotide
```

```
<400> SEQUENCE: 4
gagaggcccc cggc                                                      14

<210> SEQ ID NO 5
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 5
tgaaggccgc aaca                                                      14

<210> SEQ ID NO 6
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 6
agaaggccca tcat                                                      14

<210> SEQ ID NO 7
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 7
tagtttaaac cgtt                                                      14

<210> SEQ ID NO 8
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 8 gggggggccta tttt                                                     14

<210> SEQ ID NO 9
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 9
gatgggcctc cacc                                                      14

<210> SEQ ID NO 10
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 10
ggaggtacgg tgcc                                                      14

<210> SEQ ID NO 11
<211> LENGTH: 14
```

<212> TYPE: DNA
<213> ORGANISM: Artificial Sequence
<220> FEATURE:
<223> OTHER INFORMATION: Synthetic polynucleotide

<400> SEQUENCE: 11
gagaggcccc cggc                                                        14

<210> SEQ ID NO 12
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 12
cgggggacaa tagg                                                        14

<210> SEQ ID NO 13
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 13 gggggggccac gcgc                                                       14

<210> SEQ ID NO 14
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 14
tagtggctac catg                                                        14

<210> SEQ ID NO 15
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 15
agggggccta taat                                                        14

<210> SEQ ID NO 16
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 16
accaggccaa gtat                                                        14

<210> SEQ ID NO 17
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 17
acaaggccca taat                                              14

<210> SEQ ID NO 18
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 18
aacaggcctt aatt                                              14

<210> SEQ ID NO 19
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 19
actcggcctg aact                                              14

<210> SEQ ID NO 20
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 20 aagggccta taat                                               14

<210> SEQ ID NO 21
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 21
agtaggcctt tcat                                              14

<210> SEQ ID NO 22
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 22
acggggccta atat                                              14

<210> SEQ ID NO 23
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 23
aaacggccca ctgt                                              14

<210> SEQ ID NO 24
<211> LENGTH: 14
<212> TYPE: DNA
<213> ORGANISM: Artificial Sequence

```
<220> FEATURE:
<223> OTHER INFORMATION: Synthetic polynucleotide

<400> SEQUENCE: 24
atagggccat ccat                                                   14

<210> SEQ ID NO 25
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 25
aataggccac ttat                                                   14

<210> SEQ ID NO 26
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 26
agagggccgg gcgt                                                   14

<210> SEQ ID NO 27
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 27
agtgggccag cctt                                                   14

<210> SEQ ID NO 28
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 28
acccggccat tcat                                                   14

<210> SEQ ID NO 29
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 29
aaccggcccc gagt                                                   14

<210> SEQ ID NO 30
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 30
aaagggccag gcat                                                   14
```

<210> SEQ ID NO 31
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 31
aataggccca gact                                                        14

<210> SEQ ID NO 32
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 32
aataggcccg cagt                                                        14

<210> SEQ ID NO 33
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 33
aaatggccgg caat                                                        14

<210> SEQ ID NO 34
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 34
gacgggccta atat                                                        14

<210> SEQ ID NO 35
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 35
gcgaggccta ctat                                                        14

<210> SEQ ID NO 36
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 36
gcagggcctc attt                                                        14

<210> SEQ ID NO 37
<211> LENGTH: 14
<212> TYPE: DNA
<213> ORGANISM: Artificial Sequence
<220> FEATURE:
<223> OTHER INFORMATION: Synthetic polynucleotide

```
<400> SEQUENCE: 37
gattggccat acat                                                         14

<210> SEQ ID NO 38
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 38
ggttggccta atat                                                         14

<210> SEQ ID NO 39
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 39
ggacggccaa gcat                                                         14

<210> SEQ ID NO 40
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 40
ggcaggcctc ttct                                                         14

<210> SEQ ID NO 41
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 41
gttcggcccc gact                                                         14

<210> SEQ ID NO 42
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 42
gtacggccca taat                                                         14

<210> SEQ ID NO 43
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 43
gtatggcctc ggat                                                         14

<210> SEQ ID NO 44
```

```
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 44
gccgggcctt tttt                                                        14

<210> SEQ ID NO 45
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 45
ggccggccaa gcat                                                        14

<210> SEQ ID NO 46
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 46
gactggccta taat                                                        14

<210> SEQ ID NO 47
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 47
ggacggccta caat                                                        14

<210> SEQ ID NO 48
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 48
gggaggccag cgat                                                        14

<210> SEQ ID NO 49
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 49
gtaaggccgc cgat                                                        14

<210> SEQ ID NO 50
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 50
```
gattggccta cggt                                                    14

<210> SEQ ID NO 51
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 51
gatcggccat agat                                                    14

<210> SEQ ID NO 52
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 52
gctgggccct tccc                                                    14

<210> SEQ ID NO 53
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 53
gtcaggccta tacc                                                    14

<210> SEQ ID NO 54
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 54
gtccggcccc acac                                                    14

<210> SEQ ID NO 55
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 55
ggtcggccag tagc                                                    14

<210> SEQ ID NO 56
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 56
gttgggccgc ggac                                                    14

<210> SEQ ID NO 57
<211> LENGTH: 14
<212> TYPE: DNA

```
<213> ORGANISM: Artificial Sequence
<220> FEATURE:
<223> OTHER INFORMATION: Synthetic polynucleotide

<400> SEQUENCE: 57
gattggccag caac                                                       14

<210> SEQ ID NO 58
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 58 gggggggccga atac                                                      14

<210> SEQ ID NO 59
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 59
ggacggccct gtgc                                                       14

<210> SEQ ID NO 60
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 60
gcagggcctc taac                                                       14

<210> SEQ ID NO 61
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 61
gagcggccac aacc                                                       14

<210> SEQ ID NO 62
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 62
gcgtggccct tccc                                                       14

<210> SEQ ID NO 63
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 63
gataggccag ttac                                                       14
```

<210> SEQ ID NO 64
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 64
ggaaggcctt atac                                                    14

<210> SEQ ID NO 65
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 65
gcatggccta ctcc                                                    14

<210> SEQ ID NO 66
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 66
gataggccaa cacc                                                    14

<210> SEQ ID NO 67
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 67
gaccggcccc ccgc                                                    14

<210> SEQ ID NO 68
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 68
gattggccgc aacc                                                    14

<210> SEQ ID NO 69
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 69
gcaaggccaa cacc                                                    14

<210> SEQ ID NO 70
<211> LENGTH: 74
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<222> LOCATION: (40)..(45)
<223> OTHER INFORMATION: n is a, c, g, or t

<400> SEQUENCE: 70
ggtataatac tagtatgata aagctgctgc aatagttttn nnnnatacc agcttcgaaa      60 gaagcccttg gcag      74

<210> SEQ ID NO 71
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(41)
<223> OTHER INFORMATION: n is a, c, g, or t

<400> SEQUENCE: 71
tttttcaagt tgataacgga ctagccttat tttnnnnnnnn nctgccaagg gcttctttcg      60
aagctg      66

<210> SEQ ID NO 72
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 72
aaaactattg cagcagcttt atcatactag tattatacc      39

<210> SEQ ID NO 73
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 73
aaaataaggc tagtccgtta tcaacttgaa aaag      34

<210> SEQ ID NO 74
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 74
atgataaagc tgctgcaata gtttagagc tagaaatagc aagttaaaat aaggctagtc      60
cgttatcaac ttgaaaaagt ggcaccgagt cggtgccagc agctttatca tataccacgc      120
gaaagcgcct tggcagatga taaagttttt tt      152

<210> SEQ ID NO 75
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 75
ctaaggatga tttctggaat tc                                    22

<210> SEQ ID NO 76
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 76
cagaacgcag aagcg                                            15

<210> SEQ ID NO 77
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 77
augauaaagc ugcugcaaua                                       20

<210> SEQ ID NO 78
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 78
gaucagcggc aaugugccgc                                       20

<210> SEQ ID NO 79
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 79
guucaccaau caaauucacg                                       20

<210> SEQ ID NO 80
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 80
gaccgcgacu uccagugaag                                       20

<210> SEQ ID NO 81
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 81
cauaacgaac gcgaucgagc                                       20

<210> SEQ ID NO 82
<211> LENGTH: 20
<212> TYPE: RNA

```
<213> ORGANISM: Artificial Sequence
<220> FEATURE:
<223> OTHER INFORMATION: Synthetic polynucleotide

<400> SEQUENCE: 82
gaccaggaug ggcaccaccc                                                    20

<210> SEQ ID NO 83
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 83
ccaagctgaa ggtgaccaa                                                     19

<210> SEQ ID NO 84
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 84
ccgcagggtg ccgggttaag ttcttccgct tcactggaag tcgcggtcgg aacggtattg        60
cagcagcttt aacatctgcc gctggacggc gcacaaatcg cgcttaacgg tcaggaagca       120

<210> SEQ ID NO 85
<211> LENGTH: 146
<212> TYPE: DNA
<213> ORGANISM: Artificial Sequence
<220> FEATURE:
<223> OTHER INFORMATION: Synthetic polynucleotide

<400> SEQUENCE: 85
gagcaccgcc ttcgtctgtc gagataggac atctgcaact cgtaacaac agcttcggcg         60 gcgtggacat ggtgatcagc ggctaataac cacaaggtgc cgggttaagt tcttccgctt       120
cactggaagt cgcggtcgga accgta                                            146

<210> SEQ ID NO 86
<211> LENGTH: 146
<212> TYPE: DNA
<213> ORGANISM: Artificial Sequence
<220> FEATURE:
<223> OTHER INFORMATION: Synthetic polynucleotide

<400> SEQUENCE: 86
gagcaccgcc ttcgtcagat ctgtagtcct ctgtttgcca acgcatttgg ctaccctgcc        60
actcacacca ttcaggcgcc tggccgtgtt aataaattg gtgaacacac cgactacaac        120
gacggtttcg ttctgccctg cgcgat                                            146

<210> SEQ ID NO 87
<211> LENGTH: 147
<212> TYPE: DNA
<213> ORGANISM: Artificial Sequence
<220> FEATURE:
<223> OTHER INFORMATION: Synthetic polynucleotide

<400> SEQUENCE: 87
aagagcaccg ccttcgtcgc taagtctgac tcggcggcgt ggacatggtg atcagcggca        60
atgtgccgca gggtgccggg ttaagttctt aataaagcct ggaagtcgcg gtcggaaccg       120
```

```
tattgcagca gctttatcat ctgccgc                                        147

<210> SEQ ID NO 88
<211> LENGTH: 118
<212> TYPE: DNA
<213> ORGANISM: Artificial Sequence
<220> FEATURE:
<223> OTHER INFORMATION: Synthetic polynucleotide

<400> SEQUENCE: 88
catcacccgc ggcattacct gattatggag ttcaatatgc aagcctattt tgaccaatta    60
gactaataac gttatgaagg ctcaaaatcc tcaaacccgt tagcattccg tcactaca    118

<210> SEQ ID NO 89
<211> LENGTH: 30
<212> TYPE: RNA
<213> ORGANISM: Artificial Sequence
<220> FEATURE:
<223> OTHER INFORMATION: Synthetic polynucleotide

<400> SEQUENCE: 89
guuuuagagc uagaaauagc aaguuaaaau                                     30

<210> SEQ ID NO 90
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(7)
<223> OTHER INFORMATION: n is a, c, g, or u
<220> FEATURE:
<221> NAME/KEY: misc_feature
<222> LOCATION: (37)..(44)
<223> OTHER INFORMATION: n is a, c, g, or u

<400> SEQUENCE: 90
unnnnnnaua ccagcuucga aagaagcccu uggcagnnnn nnnna                    45

<210> SEQ ID NO 91
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 91
ccgtattgca gcagctttat cat                                            23

<210> SEQ ID NO 92
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 92
cataacgaac gcgatcgagc tgg                                            23

<210> SEQ ID NO 93
<211> LENGTH: 23
<212> TYPE: DNA
<213> ORGANISM: Artificial Sequence
<220> FEATURE:
```

```
<223> OTHER INFORMATION: Synthetic polynucleotide

<400> SEQUENCE: 93
cggtattgca gcagctttaa cat                                            23

<210> SEQ ID NO 94
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 94
cataacgtta ttagtctaat tgg                                            23

<210> SEQ ID NO 95
<211> LENGTH: 29
<212> TYPE: RNA
<213> ORGANISM: Artificial Sequence
<220> FEATURE:
<223> OTHER INFORMATION: Synthetic polynucleotide

<400> SEQUENCE: 95
auaccagcuu cgaaagaagc ccuuggcag                                      29

<210> SEQ ID NO 96
<211> LENGTH: 29
<212> TYPE: RNA
<213> ORGANISM: Artificial Sequence
<220> FEATURE:
<223> OTHER INFORMATION: Synthetic polynucleotide

<400> SEQUENCE: 96
auaccagcuu cgaaagaagc cauuggcag                                      29

<210> SEQ ID NO 97
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 97
guaucgauac cagcuucgaa agaagccnuu ggcagcuuaa gcc                      43

<210> SEQ ID NO 98
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 98
agugagauac cagcuucgaa agaagccnuu ggcagcuaaa aau                      43

<210> SEQ ID NO 99
<211> LENGTH: 43
<212> TYPE: RNA
<213> ORGANISM: Artificial Sequence
```

<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 99
gagaggauac cagcuucgaa agaagccnuu ggcagccccc ggc    43

<210> SEQ ID NO 100
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 100
ugaaggauac cagcuucgaa agaagccnuu ggcagccgca aca    43

<210> SEQ ID NO 101
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 101
agaaggauac cagcuucgaa agaagccnuu ggcagcccau cau    43

<210> SEQ ID NO 102
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 102
uaguuuauac cagcuucgaa agaagccnuu ggcagaaacc guu    43

<210> SEQ ID NO 103
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 103 gggggauac cagcuucgaa agaagccnuu ggcagccuau uuu    43

<210> SEQ ID NO 104
<211> LENGTH: 43
<212> TYPE: RNA

<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 104
gaugggauac cagcuucgaa agaagccnuu ggcagccucc acc         43

<210> SEQ ID NO 105
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

<400> SEQUENCE: 105
ggaggunacg gugcc                                         15

<210> SEQ ID NO 106
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 106
gagaggauac cagcuucgaa agaagccnuu ggcagccccc ggc          43

<210> SEQ ID NO 107
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 107 cggggauac cagcuucgaa agaagccnuu ggcagacaau agg           43

<210> SEQ ID NO 108
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

```
<400> SEQUENCE: 108 gggggggncca cgcgc                                                         15

<210> SEQ ID NO 109
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 109
uaguggauac cagcuucgaa agaagccnuu ggcagcuacc aug                            43

<210> SEQ ID NO 110
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 110 aggggggauac cagcuucgaa agaagccnuu ggcagccuau aau                           43

<210> SEQ ID NO 111
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 111
accaggauac cagcuucgaa agaagccnuu ggcagccaag uau                            43

<210> SEQ ID NO 112
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 112
acaaggauac cagcuucgaa agaagccnuu ggcagcccau aau                            43

<210> SEQ ID NO 113
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
```

```
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

<400> SEQUENCE: 113
acucggnccu gaacu                                                           15

<210> SEQ ID NO 114
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

<400> SEQUENCE: 114
aaggggnccu auaau                                                           15

<210> SEQ ID NO 115
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 115
aguaggauac cagcuucgaa agaagccnuu ggcagccuuu cau                            43

<210> SEQ ID NO 116
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 116
acggggauac cagcuucgaa agaagccnuu ggcagccuaa uau                            43

<210> SEQ ID NO 117
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 117
aaacggauac cagcuucgaa agaagccnuu ggcagcccac ugu                            43
```

```
<210> SEQ ID NO 118
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 118
auagggauac cagcuucgaa agaagccnuu ggcagccauc cau            43

<210> SEQ ID NO 119
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 119
aauaggauac cagcuucgaa agaagccnuu ggcagccacu uau            43

<210> SEQ ID NO 120
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 120
agagggauac cagcuucgaa agaagccnuu ggcagccggg cgu            43

<210> SEQ ID NO 121
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 121
agugggauac cagcuucgaa agaagccnuu ggcagccagc cuu            43

<210> SEQ ID NO 122
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 122
acccggauac cagcuucgaa agaagccnuu ggcagccauu cau            43
```

```
<210> SEQ ID NO 123
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 123
aaccggauac cagcuucgaa agaagccnuu ggcagccccg agu          43

<210> SEQ ID NO 124
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 124
aaagggauac cagcuucgaa agaagccnuu ggcagccagg cau          43

<210> SEQ ID NO 125
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 125
aauaggauac cagcuucgaa agaagccnuu ggcagcccag acu          43

<210> SEQ ID NO 126
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 126
aauaggauac cagcuucgaa agaagccnuu ggcagcccgc agu          43

<210> SEQ ID NO 127
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C
```

```
<400> SEQUENCE: 127
gguuggnccu aauau                                                    15

<210> SEQ ID NO 128
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 128
ggacggauac cagcuucgaa agaagccnuu ggcagccaag cau                     43

<210> SEQ ID NO 129
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

<400> SEQUENCE: 129
ggcaggnccu cuucu                                                    15

<210> SEQ ID NO 130
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 130
gccgggauac cagcuucgaa agaagccnuu ggcagccuuu uuu                     43

<210> SEQ ID NO 131
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 131
ggccggauac cagcuucgaa agaagccnuu ggcagccaag cau                     43

<210> SEQ ID NO 132
<211> LENGTH: 15
<212> TYPE: RNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

<400> SEQUENCE: 132
gacuggnccu auaau                                                         15

<210> SEQ ID NO 133
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 133
ggacggauac cagcuucgaa agaagccnuu ggcagccuac aau                          43

<210> SEQ ID NO 134
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 134
gauuggauac cagcuucgaa agaagccnuu ggcagccuac ggu                          43

<210> SEQ ID NO 135
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 135
gaucggauac cagcuucgaa agaagccnuu ggcagccaua gau                          43

<210> SEQ ID NO 136
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 136
guccggauac cagcuucgaa agaagccnuu ggcagcccca cac                          43
```

```
<210> SEQ ID NO 137
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 137
ggucggauac cagcuucgaa agaagccnuu ggcagccagu agc        43

<210> SEQ ID NO 138
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 138
gauuggauac cagcuucgaa agaagccnuu ggcagccagc aac        43

<210> SEQ ID NO 139
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 139 gggggggauac cagcuucgaa agaagccnuu ggcagccgaa uac       43

<210> SEQ ID NO 140
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 140
gcguggauac cagcuucgaa agaagccnuu ggcagcccuu ccc        43

<210> SEQ ID NO 141
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 141
gauaggauac cagcuucgaa agaagccnuu ggcagccagu uac        43
```

```
<210> SEQ ID NO 142
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 142
ggaaggauac cagcuucgaa agaagccnuu ggcagccuua uac          43

<210> SEQ ID NO 143
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 143
gcauggauac cagcuucgaa agaagccnuu ggcagccuac ucc          43

<210> SEQ ID NO 144
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 144
gauaggauac cagcuucgaa agaagccnuu ggcagccaac acc          43

<210> SEQ ID NO 145
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 145
gaccggauac cagcuucgaa agaagccnuu ggcagccccc cgc          43

<210> SEQ ID NO 146
<211> LENGTH: 15
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C
```

<400> SEQUENCE: 146
gauuggnccg caacc        15

<210> SEQ ID NO 147
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 147
gcaaggauac cagcuucgaa agaagccnuu ggcagccaac acc        43

<210> SEQ ID NO 148
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 148
guaucgauac cagcuucgaa agaagccnuu ggcagcuuaa gcc        43

<210> SEQ ID NO 149
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 149
gagaggauac cagcuucgaa agaagccnuu ggcagccccc ggc        43

<210> SEQ ID NO 150
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 150
ugaaggauac cagcuucgaa agaagccnuu ggcagccgca aca        43

<210> SEQ ID NO 151
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)

<223> OTHER INFORMATION: n is A or C

<400> SEQUENCE: 151
uaguuuauac cagcuucgaa agaagccnuu ggcagaaacc guu                43

<210> SEQ ID NO 152
<211> LENGTH: 42
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(27)
<223> OTHER INFORMATION: n is a, c, g, or u
<220> FEATURE:
<221> NAME/KEY: misc_feature
<222> LOCATION: (28)..(28)
<223> OTHER INFORMATION: n is A or C

<400> SEQUENCE: 152
gggggauacc agcuucgaaa gaagccnuug gcagccuauu uu                 42

<210> SEQ ID NO 153
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 153
ggagguauac cagcuucgaa agaagccnuu ggcagacggu gcc                43

<210> SEQ ID NO 154
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 154
gagaggauac cagcuucgaa agaagccnuu ggcagccccc ggc                43

<210> SEQ ID NO 155
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 155
cgggggauac cagcuucgaa agaagccnuu ggcagacaau agg                43

<210> SEQ ID NO 156
<211> LENGTH: 43
<212> TYPE: RNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 156 gggggauac cagcuucgaa agaagccnuu ggcagccacg cgc            43

<210> SEQ ID NO 157
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is the small-molecule-binding aptamer
      sequence
<220> FEATURE:
<221> NAME/KEY: misc_feature
<222> LOCATION: (28)..(28)
<223> OTHER INFORMATION: n is A or C

<400> SEQUENCE: 157
uaguggauac cagcuucgaa agaagccnuu ggcagcuacc aug            43

<210> SEQ ID NO 158
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 158
acaaggauac cagcuucgaa agaagccnuu ggcagcccau aau            43

<210> SEQ ID NO 159
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 159
acucggauac cagcuucgaa agaagccnuu ggcagccuga acu            43

<210> SEQ ID NO 160
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 160
aaggggauac cagcuucgaa agaagccnuu ggcagccuau aau            43
```

<210> SEQ ID NO 161
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 161
aguaggauac cagcuucgaa agaagccnuu ggcagccuuu cau            43

<210> SEQ ID NO 162
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 162
acggggauac cagcuucgaa agaagccnuu ggcagccuaa uau            43

<210> SEQ ID NO 163
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 163
gaucggauac cagcuucgaa agaagccnuu ggcagccaua gau            43

<210> SEQ ID NO 164
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 164 gggggauac cagcuucgaa agaagccnuu ggcagccgaa uac            43

<210> SEQ ID NO 165
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 165
ggaaggauac cagcuucgaa agaagccnuu ggcagccuua uac                                43

<210> SEQ ID NO 166
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 166
gauaggauac cagcuucgaa agaagccnuu ggcagccaac acc                                43

<210> SEQ ID NO 167
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(28)
<223> OTHER INFORMATION: n is A or C

<400> SEQUENCE: 167
gcaaggauac cagcuucgaa agaagccnuu ggcagccaac acc                                43

<210> SEQ ID NO 168
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (38)..(42)
<223> OTHER INFORMATION: n is A, C, G or U

<400> SEQUENCE: 168
gnnncgauac cagcuucgaa agaagccnuu ggcagcunnn nnc                                43

<210> SEQ ID NO 169
<211> LENGTH: 43
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (38)..(42)
<223> OTHER INFORMATION: n is A, C, G, or U

<400> SEQUENCE: 169
gnnnggauac cagcuucgaa agaagccnuu ggcagccnnn nnc       43

<210> SEQ ID NO 170
<211> LENGTH: 43
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (38)..(42)
<223> OTHER INFORMATION: n is A, C, G, or U

<400> SEQUENCE: 170
gnnnggauac cagcuucgaa agaagccnuu ggcagccnnn nnu       43

<210> SEQ ID NO 171
<211> LENGTH: 43
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (37)..(42)
<223> OTHER INFORMATION: n is A, C, G, or U

<400> SEQUENCE: 171
gnnnguauac cagcuucgaa agaagccnuu ggcagannnn nnc       43

<210> SEQ ID NO 172
<211> LENGTH: 43
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (38)..(42)
<223> OTHER INFORMATION: n is A, C, G, or U

<400> SEQUENCE: 172
annnggauac cagcuucgaa agaagccnuu ggcagccnnn nnu       43

<210> SEQ ID NO 173
<211> LENGTH: 43
<212> TYPE: RNA

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (37)..(42)
<223> OTHER INFORMATION: n is A, C, G, or U

<400> SEQUENCE: 173
cnnnggauac cagcuucgaa agaagccnuu ggcagannnn nng            43

<210> SEQ ID NO 174
<211> LENGTH: 41
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (36)..(40)
<223> OTHER INFORMATION: n is A, C, G, or U

<400> SEQUENCE: 174
unnnggauac cagcuucgaa agaagccnuu ggcagnnnnn a              41

<210> SEQ ID NO 175
<211> LENGTH: 41
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (36)..(40)
<223> OTHER INFORMATION: n is A, C, G, or U

<400> SEQUENCE: 175
unnnggauac cagcuucgaa agaagccnuu ggcagnnnnn g              41

<210> SEQ ID NO 176
<211> LENGTH: 41
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is A, C, G, or U
```

```
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (36)..(40)
<223> OTHER INFORMATION: n is A, C, G, or U

<400> SEQUENCE: 176
unnnuuauac cagcuucgaa agaagccnuu ggcagnnnnn u                41

<210> SEQ ID NO 177
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (38)..(42)
<223> OTHER INFORMATION: n is A, C, G, or U

<400> SEQUENCE: 177
gnnnggauac cagcuucgaa agaagccnuu ggcagccnnn nnu              43

<210> SEQ ID NO 178
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(6)
<223> OTHER INFORMATION: n is A, C, G, or U
<220> FEATURE:
<221> NAME/KEY: misc_feature
<222> LOCATION: (28)..(28)
<223> OTHER INFORMATION: n is A or C
<220> FEATURE:
<221> NAME/KEY: misc_feature
<222> LOCATION: (35)..(42)
<223> OTHER INFORMATION: n is A, C, G, or U
<220> FEATURE:
<221> NAME/KEY: misc_feature
<222> LOCATION: (43)..(43)
<223> OTHER INFORMATION: n is a, c, g, or u

<400> SEQUENCE: 178
nnnnnnauac cagcuucgaa agaagccnuu ggcagnnnnn nnn              43

<210> SEQ ID NO 179
<211> LENGTH: 1368
<212> TYPE: PRT
<213> ORGANISM: Artificial Sequence
<220> FEATURE:
<223> OTHER INFORMATION: Cas9 amino acid sequence

<400> SEQUENCE: 179

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
```

-continued

```
                20                  25                  30
Lys Val Leu Gly Asn Thr Asp Arg His Ser Ile Lys Lys Asn Leu Ile
            35                  40                  45
Gly Ala Leu Leu Phe Asp Ser Gly Glu Thr Ala Glu Ala Thr Arg Leu
        50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Gly Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
                785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860
```

-continued

```
Gly Lys Ser Asp Asn Val Pro Ser Glu Glu Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
```

```
            1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
1355                1360                1365

<210> SEQ ID NO 180
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 180
gagaggugaa gaauacgacc accuagguag aaauaccuaa aacauac                47

<210> SEQ ID NO 181
<211> LENGTH: 29
<212> TYPE: RNA
<213> ORGANISM: Artificial Sequence
<220> FEATURE:
<223> OTHER INFORMATION: Synthetic - Aptamer 1/2 Consensus
<220> FEATURE:
<221> NAME/KEY: misc_feature
<222> LOCATION: (22)..(22)
<223> OTHER INFORMATION: n is A or C

<400> SEQUENCE: 181
auaccagcuu cgaaagaagc cnuuggcag                                    29

<210> SEQ ID NO 182
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is a, c, g, or u
<220> FEATURE:
<221> NAME/KEY: misc_feature
<222> LOCATION: (38)..(42)
<223> OTHER INFORMATION: n is a, c, g, or u

<400> SEQUENCE: 182
gnnnggauac cagcuucgaa agaagcccuu ggcagccnnn nnc                    43

<210> SEQ ID NO 183
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is a, c, g, or u
```

```
<220> FEATURE:
<221> NAME/KEY: misc_feature
<222> LOCATION: (38)..(42)
<223> OTHER INFORMATION: n is a, c, g, or u

<400> SEQUENCE: 183
annnggauac cagcuucgaa agaagcccuu ggcagccnnn nnu          43

<210> SEQ ID NO 184
<211> LENGTH: 43
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (2)..(4)
<223> OTHER INFORMATION: n is a, c, g, or u
<220> FEATURE:
<221> NAME/KEY: misc_feature
<222> LOCATION: (38)..(42)
<223> OTHER INFORMATION: n is a, c, g, or u

<400> SEQUENCE: 184
gnnnggauac cagcuucgaa agaagcccuu ggcagccnnn nnu          43

<210> SEQ ID NO 185
<211> LENGTH: 43
<212> TYPE: RNA
<213> ORGANISM: Artificial Sequence
<220> FEATURE:
<223> OTHER INFORMATION: Synthetic polynucleotide

<400> SEQUENCE: 185
agagcuauac cagcuucgaa agaagcccuu ggcagagcaa guu          43

<210> SEQ ID NO 186
<211> LENGTH: 43
<212> TYPE: RNA
<213> ORGANISM: Artificial Sequence
<220> FEATURE:
<223> OTHER INFORMATION: Synthetic polynucleotide

<400> SEQUENCE: 186
ugaaggauac cagcuucgaa agaagcccuu ggcagccgca aca          43

<210> SEQ ID NO 187
<211> LENGTH: 43
<212> TYPE: RNA
<213> ORGANISM: Artificial Sequence
<220> FEATURE:
<223> OTHER INFORMATION: Synthetic polynucleotide

<400> SEQUENCE: 187
gaucggauac cagcuucgaa agaagcccuu ggcagccaaa gau          43

<210> SEQ ID NO 188
<211> LENGTH: 43
<212> TYPE: RNA
<213> ORGANISM: Artificial Sequence
<220> FEATURE:
<223> OTHER INFORMATION: Synthetic polynucleotide

<400> SEQUENCE: 188
gggggGauac cagcuucgaa agaagcccuu ggcagccuau uuu          43
```

COMPOSITIONS AND METHODS OF USE FOR SMALL-MOLECULE REGULATION OF CRISPR-CAS9 ACTIVITY USING RNA APTAMERS

CROSS REFERENCE TO RELATED APPLICATIONS

This Continuation application claims priority to Patent Cooperation Treaty (PCT) Application No. PCT/US2020/013718, filed Jan. 15, 2020, which claims the benefit under 35 U.S.C. § 119(3) of the filing date of U.S. Provisional Application No. 62/793,748 filed Jan. 17, 2019. Each of these applications is hereby incorporated by reference in their entirety for all purposes.

GOVERNMENT LICENSE RIGHTS

This invention was made with government support under grant number GM073850 awarded by the National Institutes of Health. The government has certain rights in the invention.

SEQUENCE LISTING

The instant application contains a Sequence Listing which has been submitted electronically in ASCII format and is incorporated herein by reference in its entirety for all purposes. The ASCII copy, created on Oct. 28, 2024, is named 101877-696496 CU4364B-US1 Sequence_listing_ST25.txt and is 57,600 bytes in size.

BACKGROUND

CRISPR-Cas9 has led to great advances in gene editing for a broad spectrum of applications. To further the utility of Cas9, there have been efforts to achieve temporal control over its nuclease activity. While different approaches have focused on regulation of Cas9 or gRNA-regulated CRISPR interference, none of the reported methods enable stringent control of the nuclease activity in an orthogonal and multiplexed manner. As a result, there remains a need for improved methods to temporally control Cas9 activity.

SUMMARY

Provided herein are compositions and methods for temporal regulation of Cas enzyme activity, as well as methods of selecting compositions for the temporal regulation of Cas enzyme activity. Described herein is single guide RNA (sgRNA) that comprises a small-molecule-binding aptamer at a specific location, which enables small-molecule-dependent gene editing in bacteria. In some embodiments, the sgRNA comprises specific linking RNA sequences positioned between the sgRNA and the aptamer. Also described herein is a method for selecting sgRNAs that allow for small-molecule dependent gene editing in bacterium.

Accordingly, in some aspects, the disclosure provides a single guide RNA (sgRNA) comprising a small-molecule-binding aptamer sequence adjacent to a region comprising a 2×4 internal loop and upper stem.

In some embodiments, the small-molecule-binding aptamer is a theophylline-binding aptamer or 3-methylxanthine-binding aptamer. In some embodiments, the small-molecule-binding aptamer is a theophylline-binding aptamer and the theophylline-binding aptamer comprises the sequence 5'-AUACCAGCUUCGAAAGAAGCCCUUGGCAG-3' (SEQ ID NO: 95). In some embodiments, the small-molecule-binding aptamer is a 3-methylxanthine-binding aptamer and the 3-methylxanthine-binding aptamer comprises the sequence 5'-AUACCAGCUUCGAAAGAAGCCAUUGGCAG-3' (SEQ ID NO: 96).

In some embodiments, sgRNA contains 0-2 nucleotides between the small-molecule-binding aptamer sequence and the 2×4 internal loop and upper stem, optionally wherein the sgRNA contains 0 nucleotides between the small-molecule-binding aptamer sequence and the 2×4 internal loop and upper stem.

In some embodiments, the region comprising the 2×4 internal loop and upper stem comprises the sequence 5'-GNNNCGXCUNNNNNC-3'(SEQ ID NO: 168), 5'-GNNNGGXCCNNNNNC-3' (SEQ ID NO: 169), 5'-GNNNGGXCCNNNNNU-3'(SEQ ID NO: 170), 5'-GNNNGUXANNNNNNC-3'(SEQ ID NO: 171), 5'-ANNNGGXCCNNNNNU-3'(SEQ ID NO: 172), 5'-CNNNGGXANNNNNNG-3'(SEQ ID NO: 173), 5'-UNNNGGXNNNNNA-3' (SEQ ID NO: 174), 5'-UNNNGGXNNNNNG-3 (SEQ ID NO: 175)', 5'-UNNNUUXNNNNNNU-3' (SEQ ID NO: 176) or 5'-GNNNGGXCCNNNNNU-3' (SEQ ID NO: 177), wherein N is any nucleotide and wherein X is the small-molecule-binding aptamer sequence.

In some embodiments, the region comprising the 2×4 internal loop and upper stem comprises any one of the sequences in Table 1, wherein X in Table 1 is the small-molecule-binding aptamer sequence:

TABLE 1

| Clone Name | Sequence (5' To 3') | SEQ ID NO: |
|---|---|---|
| G1B1 | GUAUCGXCUUAAGCC | 97 |
| RG53 | AGUGAGXCUAAAAAU | 98 |
| A38 | GAGAGGXCCCCCGGC | 99 |
| A9 | UGAAGGXCCGCAACA | 100 |
| A39 | AGAAGGXCCCAUCAU | 101 |
| A34 | UAGUUUXAAACCGUU | 102 |
| A1 | GGGGGGXCCUAUUUU | 103 |
| A10 | GAUGGGXCCUCCACC | 104 |
| A14 | GGAGGUXACGGUGCC | 105 |
| A19 | GAGAGGXCCCCCGGC | 106 |
| A8 | CGGGGGXACAAUAGG | 107 |
| A26 | GGGGGGXCCACGCGC | 108 |
| C2A2 | UAGUGGXCUACCAUG | 109 |
| AU1 | AGGGGGXCCUAUAAU | 110 |
| AU2 | ACCAGGXCCAAGUAU | 111 |
| AU3 | ACAAGGXCCCAUAAU | 112 |
| AU5 | ACUCGGXCCUGAACU | 113 |
| AU6 | AAGGGGXCCUAUAAU | 114 |
| AU7 | AGUAGGXCCUUUCAU | 115 |
| AU8 | ACGGGGXCCUAAUAU | 116 |
| AU9 | AAACGGXCCCACUGU | 117 |
| AU10 | AUAGGGXCCAUCCAU | 118 |

TABLE 1-continued

| Clone Name | Sequence (5' To 3') | SEQ ID NO: |
|---|---|---|
| AU11 | AAUAGGXCCACUUAU | 119 |
| AU12 | AGAGGGXCCGGGCGU | 120 |
| AU14 | AGUGGGXCCAGCCUU | 121 |
| AU15 | ACCCGGXCCAUUCAU | 122 |
| AU16 | AACCGGXCCCCGAGU | 123 |
| AU17 | AAAGGGXCCAGGCAU | 124 |
| AU18 | AAUAGGXCCCAGACU | 125 |
| AU19 | AAUAGGXCCCGCAGU | 126 |
| GU5 | GGUUGGXCCUAAUAU | 127 |
| GU6 | GGACGGXCCAAGCAU | 128 |
| GU8 | GGCAGGXCCUCUUCU | 129 |
| GU12 | GCCGGGXCCUUUUUU | 130 |
| GU13 | GGCCGGXCCAAGCAU | 131 |
| GU14 | GACUGGXCCUAUAAU | 132 |
| GU15 | GGACGGXCCUACAAU | 133 |
| GU18 | GAUUGGXCCUACGGU | 134 |
| GU19 | GAUCGGXCCAUAGAU | 135 |
| GC3 | GUCCGGXCCCCACAC | 136 |
| GC4 | GGUCGGXCCAGUAGC | 137 |
| GC6 | GAUUGGXCCAGCAAC | 138 |
| GC7 | GGGGGGXCCGAAUAC | 139 |
| GC11 | GCGUGGXCCCUUCCC | 140 |
| GC12 | GAUAGGXCCAGUUAC | 141 |
| GC13 | GGAAGGXCCUUAUAC | 142 |
| GC15 | GCAUGGXCCUACUCC | 143 |
| GC16 | GAUAGGXCCAACACC | 144 |
| GC17 | GACCGGXCCCCCCGC | 145 |
| GC18 | GAUUGGXCCGCAACC | 146 |
| GC20 | GCAAGGXCCAACACC | 147 |

In some embodiments, the region comprising the 2×4 internal loop and upper stem comprises any one of the sequences in Table 2, wherein X in Table 2 is the small-molecule-binding aptamer sequence:

TABLE 2

| Clone Name | Sequence (5' To 3') | SEQ ID NO: |
|---|---|---|
| G1B1 | GUAUCGXCUUAAGCC | 148 |
| A38 | GAGAGGXCCCCCGGC | 149 |
| A9 | UGAAGGXCCGCAACA | 150 |

TABLE 2-continued

| Clone Name | Sequence (5' To 3') | SEQ ID NO: |
|---|---|---|
| A34 | UAGUUUXAAACCGUU | 151 |
| A1 | GGGGGGXCCUAUUUU | 152 |
| A14 | GGAGGUXACGGUGCC | 153 |
| A19 | GAGAGGXCCCCCGGC | 154 |
| A8 | CGGGGGXACAAUAGG | 155 |
| A26 | GGGGGGXCCACGCGC | 156 |
| C2A2 | UAGUGGXCUACCAUG | 157 |
| AU3 | ACAAGGXCCCAUAAU | 158 |
| AU5 | ACUCGGXCCUGAACU | 159 |
| AU6 | AAGGGGXCCUAUAAU | 160 |
| AU7 | AGUAGGXCCUUUCAU | 161 |
| AU8 | ACGGGGXCCUAAUAU | 162 |
| GU19 | GAUCGGXCCAUAGAU | 163 |
| GC7 | GGGGGGXCCGAAUAC | 164 |
| GC13 | GGAAGGXCCUUAUAC | 165 |
| GC16 | GAUAGGXCCAACACC | 166 |
| GC20 | GCAAGGXCCAACACC | 167 |

In some embodiments, the region comprising the 2×4 internal loop and upper stem comprises the sequence 5'-GGGGGGXCCUAUUUU-3'(SEQ ID NO: 103), 5'-UGAAGGXCCGCAACA-3' (SEQ ID NO: 100) or 5'-GAUCGGXCCAUAGAU-3' (SEQ ID NO: 135).

In other aspects, the disclosure provides a ribonucleoprotein (RNP) comprising a sgRNA of any one of the above embodiments or as otherwise described herein and a Cas enzyme. In some embodiments, the Cas enzyme is Cas9.

In other aspects, the disclosure provides a method of inducing gene editing in a bacterium, the method comprising (a) introducing or expressing in a bacterium the sgRNA of any one of the above embodiments or as otherwise described herein, (b) introducing or expressing a Cas enzyme in the bacterium, and (c) contacting the bacterium with a small molecule that interacts with the small-molecule-binding aptamer sequence in the sgRNA such that gene editing is induced in the bacterium. In some embodiments, the small molecule is theophylline or 3-methylxanthine. In some embodiments, the method comprises introducing at least two sgRNAs into the bacterium, wherein a first sgRNA comprises a first small-molecule-binding aptamer sequence and a second sgRNA comprises a second small-molecule-binding aptamer sequence that is different than the first small-molecule-binding aptamer sequence, and wherein the method comprises contacting the bacterium with a first small molecule that interacts with the first small-molecule-binding aptamer sequence and contacting the bacterium with a second small molecule that interacts with the second small-molecule-binding aptamer sequence. In some embodiments, the bacterium is contacted with the first small molecule prior to the second small molecule, or vice versa. In some embodiments, the first small molecule is theophylline and the second small molecule is 3-methylxanthine. In some embodiments, the Cas enzyme is Cas9.

In yet other aspects, the disclosure provides an in vivo method of selecting a switchable aptamer single guide RNA (agRNA) that is inducible with a small molecule, the method comprising (a) performing a negative selection step comprising growing a first plurality of bacteria in the absence of the small molecule and in the absence of λ-red protein expression, thereby inducing cell death in a subset of the plurality to produce a second plurality of bacteria, wherein individual bacteria in the first plurality comprise a nucleic acid encoding a candidate agRNA that produces a cut site in the gene encoding a selection marker protein, a Cas enzyme, and a template for homologous repair of the cut site in the gene that encodes the selection marker protein; (b) performing a positive selection step comprising either (i) growing the second plurality of bacteria in the presence of the small molecule and λ-red protein expression or (ii) isolating nucleic acids encoding candidate agRNAs from the second plurality of bacteria and introducing the nucleic acids into a third plurality of bacteria and growing the third plurality of bacteria in the presence of the small molecule and λ-red protein expression, wherein individual bacteria in the third plurality comprise a nucleic acid encoding a candidate agRNA that produces a cut site in the gene encoding a selection marker protein, a Cas enzyme, and a template for homologous repair of the cut site in the gene that encodes the selection marker protein; and (c) selecting at least one bacterium from step (b) that expresses the altered selection marker protein. In some embodiments, the selection marker protein is galK and the template for homologous repair comprises a premature stop codon for the galK gene. In some embodiments, the bacteria is E. coli.

In yet other aspects, the disclosure provides in vivo method of selecting a switchable aptamer single guide RNA (agRNA) that is inducible with a small molecule, the method comprising (a) performing a negative selection step comprising growing a first plurality of bacteria in the absence of the small molecule and in the presence of λ-red protein expression, thereby inducing cell death in a subset of the plurality to produce a second plurality of bacteria, wherein individual bacteria in the first plurality comprise a nucleic acid encoding a candidate agRNA that produces a cut site in the gene encoding a selection marker protein, a Cas enzyme, and a template for homologous repair of the cut site in the gene that encodes the selection marker protein; (b) performing a positive selection step comprising either (i) growing the second plurality of bacteria in the presence of the small molecule and λ-red protein expression or (ii) isolating nucleic acids encoding candidate agRNAs from the second plurality of bacteria and introducing the nucleic acids into a third plurality of bacteria and growing the third plurality of bacteria in the presence of the small molecule and λ-red protein expression, wherein individual bacteria in the third plurality comprise a nucleic acid encoding a candidate agRNA that produces a cut site in the gene encoding a selection marker protein, a Cas enzyme, and a template for homologous repair of the cut site in the gene that encodes the selection marker protein; and (c) selecting at least one bacterium from step (b) that expresses the altered selection marker protein. In some embodiments, the selection marker protein is galK and the template for homologous repair comprises a premature stop codon for the galK gene. In some embodiments, the bacteria is E. coli.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1A shows that the theophylline aptamer is inserted into the sgRNA at the site of the tetraloop used to fuse the guide and tracrRNAs. FIG. 1B shows that the 2×4 internal loop and flanking helices were randomized to yield agRNA libraries. FIG. 1C is a schematic showing that the switchable constructs were enriched in the two steps of the galK survival selection. FIG. 1D is an overview of constructs that were sampled from the enriched plasmid library after the galK survival selection. Editing was induced with 1 mM theophylline. The outer graph shows agRNAs are binned according to the difference in editing efficiency in an induced and uninduced population. The inset graph shows agRNAs are binned according to the fold increase in editing efficiency upon induction. FIG. 1E is a graph showing inducible gene editing was tested at sites other than the canonical galK1 site used for the galK selection (full circles, 1 mM theophylline added; empty circles, no theophylline added). The error bars represent the standard deviation from the mean.

FIG. 2A is a heat map of the editing efficiency at the galK1 site with the agRNAs A9 and GU19 as a function of the concentration of theophylline and the time of recovery with theophylline after transformation. In FIGS. 2A-2B, the values represent the average of three biological replicates. FIG. 2B shows the editing efficiency at the galK1 site was measured for agRNAs composed of the theophylline or 3MX-aptamer coupled via the linker A9 or GU19 in dependence of 1 mM theophylline (Theo) or 1 mM 3MX. Recovery time was 3 hours. FIG. 2C shows the binding of Cas9 to sgRNA or agRNAs was observed and quantified via EMSA. Two representative binding curves for the A9 agRNA with and without 250 µM theophylline are displayed. The inset table summarizes all measured dissociation constants. Error bars indicate standard deviation from the mean.

FIG. 3A is a schematic showing the workflow of the aptamer-controlled gene editing. In the left graph, FIG. 3B shows the transformation efficiencies of the MGλ9 strain with wt gRNA and agRNAs that are activated with theophylline 1 hour after transformation. CFUs are colony forming units µg-1 DNA and per 4 mL of recovery media. In the right graph, FIG. 3B shows the editing efficiencies with wt gRNA and ligand-activatable agRNAs that are activated with theophylline 1 hour after transformation. Each dot represents a biological replicate and error bars indicate standard deviation from the mean. FIG. 3C is a schematic of the plasmid design used to enable multiplexed gene editing. The individual homology arms and agRNAs are identical to the ones previously described for the single-edit experiments. FIG. 3D shows the editing efficiency at the two gene sites, galK (site 1) and xylA (site 2) in dependence on agRNA induction with either 1 mM theophylline and/or 1 mM 3MX. The values represent the average of three biological replicates.

FIG. 4A is a graph showing that replacing the tetraloop in the wild-type sgRNA with the theophylline aptamer, but leaving the 2×4 loop unchanged, did not change the activity of the agRNA nor did it make the agRNA theophylline-dependent. agRNAs created by Liu et al.[8], designed to regulate gene expression via CRISPRi, lead to gene editing with and without the aptamer-ligand. Full circles: 1 mM theophylline added, empty circles: no theophylline added. FIG. 4B is a graph showing Cas9 expression was regulated by the pBAD promoter which is induced by addition of 0.2% arabinose. The number of transformants and the editing efficiency was independent of arabinose. Full circles: 0.2% (w/v) arabinose added, empty circles: no arabinose added. CFU: colony forming units. Every circle represents one biological replicate.

DETAILED DESCRIPTION

Figure 1A:
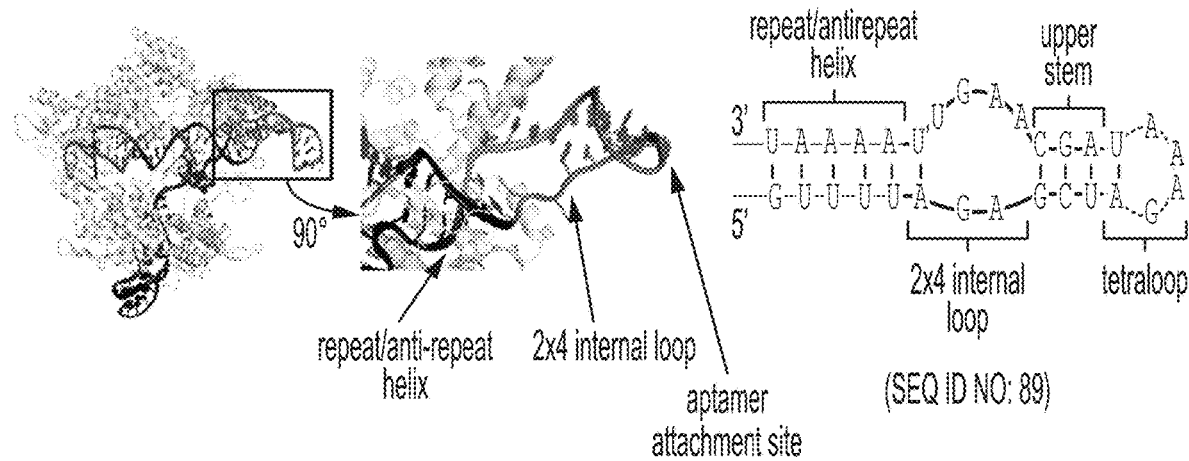
FIGS. 1A-1E show the design, selection and screening of agRNA libraries.

The utility of CRISPR for genome editing in bacteria such as *E. coli* has been demonstrated in various studies. However, CRISPR-based editing technologies in bacteria suffer from low transformation efficiencies caused by the lethality of double-stranded DNA (dsDNA) breaks in bacteria and from associated issues, such as biases in multiplexed libraries towards non-cutting gRNAs. As described herein, the tetraloop that fuses the crRNA and tracrRNA in a sgRNA was replaced with a small-molecule-binding aptamer sequence and, in some embodiments, modifications were made to the region that attaches the aptamer to the rest of the sgRNA, namely the 2×4 internal loop and upper stem. As described herein, gene editing is induced in bacteria expressing the modified sgRNAs by addition of a small molecule that interacts with the aptamer. Accordingly, the present disclosure provides compositions and methods for inducing gene editing in bacteria, e.g., in a temporally controlled manner.

Single Guide RNAs (sgRNAs)

In some aspects, the disclosure provides single guide RNAs (sgRNAs) that comprise an aptamer sequence, e.g., an aptamer sequence as described herein.

CRISPR (clustered regularly interspaced short palindromic repeats)/Cas is a prokaryotic antiviral system that has been repurposed for gene editing in a variety of cell types, including bacteria. In general, the CRISPR/Cas system relies on the activity of two RNAs, a trans-activating CRISPR RNA (tracrRNA) and a CRISPR RNA (crRNA), which interact with a Cas enzyme (e.g., Cas9) and direct the Cas enzyme to cut the genome is a site-specific manner. The crRNA portion contains a protospacer, generally 20-nucleotides long, which determines the sequence specificity of the Cas nuclease activity. In general, the protospacer should be complementary to a region in the genome that is adjacent to a protospacer adjacent motif (PAM).

The sequence of the PAM depends on the type of Cas enzyme used. PAM sequences are known in the art and further described herein. The tracrRNA contains a stem loop structure that binds to the Cas enzyme. In their natural state, the tracrRNA and crRNA are separate molecules that bind together through a base pairing interaction. A single guide RNA (sgRNA) is a single synthetic molecule that comprises both a tracrRNA and a crRNA. sgRNAs are well-known in the art (see, e.g., Jinek et al. A programmable dual-RNA-guided DNA endonuclease in adaptive bacterial immunity. Science. 2012; 337(6096):816-21) and can be ordered through commercially available vendors (e.g., Dharmacon or New England Biolabs) or designed using the methods described in the Examples and/or through available software (e.g., CHOPCHOP v2: a web tool for the next generation of CRISPR genome engineering. Nucleic Acids Res 44(W1), W272-W276 (2016) and chopchop.cbu.uib.no). Generally, in a sgRNA the tracrRNA and crRNA are connected through a tetraloop sequence, which is connected to the rest of the sgRNA through a 2×4 internal loop and an upper stem. An example structure of an sgRNA showing the tetraloop, internal loop and upper stem is provided in FIG. 1A. As described herein, the tetraloop sequence may be replaced, in whole or in part, with an aptamer sequence, e.g., a small-molecule-binding aptamer sequence, and that aptamer sequence can be used to provide an inducible sgRNA. An example structure of an sgRNA showing the aptamer, internal loop and upper stem is provided in FIG. 1B.

Accordingly, in some embodiments, the disclosure provides an sgRNA comprising an aptamer sequence as described herein, e.g., a small-molecule-binding aptamer sequence. In some embodiments, the aptamer sequence, e.g., a small-molecule-binding aptamer sequence, replaces (in whole or in part) a tetraloop in the sgRNA. In some embodiments, the aptamer sequence, e.g., a small-molecule-binding aptamer sequence, is adjacent to (e.g., within 5, 4, 3, 2, 1 or 0 nucleotides of) a region of the sgRNA comprising a 2×4 internal loop and/or upper stem. In some embodiments, the aptamer sequence, e.g., a small-molecule-binding aptamer sequence, is located in a bridging region that joins the tracrRNA and crRNA regions of the sgRNA sequence.

In some embodiments, the region comprising the 2×4 internal loop and upper stem comprises the sequence 5'-NNNNNNXNNNNNNNN-3' (SEQ ID NO: 178), wherein N is any nucleotide and wherein X is an aptamer sequence (e.g., SEQ ID NO: 95 or 96 or 180). Typically, an aptamer sequence (e.g., as represented by X) is from about 10 nucleotides to about 50 nucleotides in length, e.g., from about 20 nucleotides to 40 nucleotides in length. In some embodiments, the region comprising the 2×4 internal loop and upper stem comprises the sequence 5'-GNNNCGX-CUNNNNNC-3'(SEQ ID NO: 168), 5'-GNNNGGXCCNNNNNC-3'(SEQ ID NO: 169), 5'-GNNNGGXCCNNNNNU-3'(SEQ ID NO: 170), 5'-GNNNGUXANNNNNNC-3'(SEQ ID NO: 171), 5'-ANNNGGXCCNNNNNU-3'(SEQ ID NO: 172), 5'-CNNNGGXANNNNNNG-3'(SEQ ID NO: 173), 5'-UN-NNGGXNNNNNA-3'(SEQ ID NO: 174), 5'-UN- NNGGXNNNNNG-3' (SEQ ID NO: 175), 5'-UNNN-UUXNNNNNU-3' (SEQ ID NO: 176) or 5'-GNNNGGXCCNNNNNU-3' (SEQ ID NO: 177), wherein N is any nucleotide and wherein X is an aptamer sequence, e.g., an aptamer sequence as described herein. In some embodiments, the region comprising the 2×4 internal loop and upper stem comprises any one of the sequences in in the Examples or in Table 1 or Table 2, wherein X in Table 1 and Table 2 is an aptamer sequence, e.g., an aptamer sequence as described herein. In some embodiments, the region comprising the 2×4 internal loop and upper stem comprises any one of the sequences in in the Examples or in Table 1 or Table 2 with up to 5, 4, 3, 2 or 1 substitutions, deletions, or additions. In some embodiments, the region comprising the 2×4 internal loop and upper stem comprises the sequence 5'-GGGGGGXCCUAUUUU-3' (SEQ ID NO: 103), 5'-UGAAGGXCCGCAACA-3' (SEQ ID NO: 100) or 5'-GAUCGGXCCAUAGAU-3' (SEQ ID NO: 135). In some embodiments, the region comprising the 2×4 internal loop and upper stem comprises the sequence 5'-GGGGGGXCCUAUUUU-3' (SEQ ID NO: 103), 5'-UGAAGGXCCGCAACA-3' (SEQ ID NO: 100) or 5'-GAUCGGXCCAUAGAU-3' (SEQ ID NO: 135) with up to 5, 4, 3, 2 or 1 substitutions, deletions, or additions.

TABLE 1

Example sequences

| Clone Name | Sequence (5' To 3') | SEQ ID NO: |
|---|---|---|
| G1B1 | GUAUCGXCUUAAGCC | 97 |
| RG53 | AGUGAGXCUAAAAAU | 98 |
| A38 | GAGAGGXCCCCCGGC | 99 |
| A9 | UGAAGGXCCGCAACA | 100 |
| A39 | AGAAGGXCCCAUCAU | 101 |
| A34 | UAGUUUXAAACCGUU | 102 |
| A1 | GGGGGGXCCUAUUUU | 103 |
| A10 | GAUGGGXCCUCCACC | 104 |
| A14 | GGAGGUXACGGUGCC | 105 |
| A19 | GAGAGGXCCCCCGGC | 106 |
| A8 | CGGGGGXACAAUAGG | 107 |
| A26 | GGGGGGXCCACGCGC | 108 |
| C2A2 | UAGUGGXCUACCAUG | 109 |
| AU1 | AGGGGGXCCUAUAAU | 110 |
| AU2 | ACCAGGXCCAAGUAU | 111 |
| AU3 | ACAAGGXCCCAUAAU | 112 |
| AU5 | ACUCGGXCCUGAACU | 113 |
| AU6 | AAGGGGXCCUAUAAU | 114 |
| AU7 | AGUAGGXCCUUUCAU | 115 |
| AU8 | ACGGGGXCCUAAUAU | 116 |
| AU9 | AAACGGXCCCACUGU | 117 |
| AU10 | AUAGGGXCCAUCCAU | 118 |

TABLE 1-continued

Example sequences

| Clone Name | Sequence (5' To 3') | SEQ ID NO: |
|---|---|---|
| AU11 | AAUAGGXCCACUUAU | 119 |
| AU12 | AGAGGGXCCGGGCGU | 120 |
| AU14 | AGUGGGXCCAGCCUU | 121 |
| AU15 | ACCCGGXCCAUUCAU | 122 |
| AU16 | AACCGGXCCCCGAGU | 123 |
| AU17 | AAAGGGXCCAGGCAU | 124 |
| AU18 | AAUAGGXCCCAGACU | 125 |
| AU19 | AAUAGGXCCCGCAGU | 126 |
| GU5 | GGUUGGXCCUAAUAU | 127 |
| GU6 | GGACGGXCCAAGCAU | 128 |
| GU8 | GGCAGGXCCUCUUCU | 129 |
| GU12 | GCCGGGXCCUUUUUU | 130 |
| GU13 | GGCCGGXCCAAGCAU | 131 |
| GU14 | GACUGGXCCUAUAAU | 132 |
| GU15 | GGACGGXCCUACAAU | 133 |
| GU18 | GAUUGGXCCUACGGU | 134 |
| GU19 | GAUCGGXCCAUAGAU | 135 |
| GC3 | GUCCGGXCCCCACAC | 136 |
| GC4 | GGUCGGXCCAGUAGC | 137 |
| GC6 | GAUUGGXCCAGCAAC | 138 |
| GC7 | GGGGGGXCCGAAUAC | 139 |
| GC11 | GCGUGGXCCCUUCCC | 140 |
| GC12 | GAUAGGXCCAGUUAC | 141 |
| GC13 | GGAAGGXCCUUUAUC | 142 |
| GC15 | GCAUGGXCCUACUCC | 143 |
| GC16 | GAUAGGXCCAACACC | 144 |
| GC17 | GACCGGXCCCCCCGC | 145 |
| GC18 | GAUUGGXCCGCAACC | 146 |
| GC20 | GCAAGGXCCAACACC | 147 |

TABLE 2

Further example sequences

| Clone Name | Sequence (5' To 3') | SEQ ID NO: |
|---|---|---|
| G1B1 | GUAUCGXCUUAAGCC | 148 |
| A38 | GAGAGGXCCCCCGGC | 149 |
| A9 | UGAAGGXCCGCAACA | 150 |
| A34 | UAGUUUXAAACCGUU | 151 |

TABLE 2-continued

Further example sequences

| Clone Name | Sequence (5' To 3') | SEQ ID NO: |
|---|---|---|
| A1 | GGGGGGXCCUAUUUU | 152 |
| A14 | GGAGGUXACGGUGCC | 153 |
| A19 | GAGAGGXCCCCCGGC | 154 |
| A8 | CGGGGGXACAAUAGG | 155 |
| A26 | GGGGGGXCCACGCGC | 156 |
| C2A2 | UAGUGGXCUACCAUG | 157 |
| AU3 | ACAAGGXCCCAUAAU | 158 |
| AU5 | ACUCGGXCCUGAACU | 159 |
| AU6 | AAGGGGXCCUAUAAU | 160 |
| AU7 | AGUAGGXCCUUUCAU | 161 |
| AU8 | ACGGGGXCCUAAUAU | 162 |
| GU19 | GAUCGGXCCAUAGAU | 163 |
| GC7 | GGGGGGXCCGAAUAC | 164 |
| GC13 | GGAAGGXCCUUAUAC | 165 |
| GC16 | GAUAGGXCCAACACC | 166 |
| GC20 | GCAAGGXCCAACACC | 167 |

Aptamer

In some aspects, the disclosure provides an aptamer which is inserted into an sgRNA, e.g., an sgRNA as described herein. As used herein, an "aptamer" is an oligonucleotide molecule that binds to a target molecule. In some embodiments, the aptamer is an RNA aptamer that binds to a target molecule. In some embodiments, the target molecule is a small molecule, such that the aptamer is a small-molecule-binding aptamer. In some embodiments, the small-molecule-binding aptamer is an RNA aptamer that binds to a small molecule. In some embodiments, an aptamer (e.g., RNA aptamer) is up to about 50 nucleotides in length, e.g., up to 20 nucleotides, up to 30 nucleotides, or up to 40 nucleotides in length. In some embodiments, an aptamer (e.g., RNA aptamer) is at least 10 nucleotides in length, e.g., between 10 nucleotides to 50 nucleotides in length.

The small molecule can be any small molecule known in the art or described herein. Preferably, the small molecule is one that does not significantly negatively impact the viability of bacteria or significantly negatively impact gene editing in bacteria. In some embodiments, an aptamer can be designed and/or selected using methods known in the art (e.g., using SELEX (Systematic Evolution of Ligands by EXponential enrichment) or the methods described in Codrea et al. In Vitro Selection of RNA Aptamers to a Small Molecule Target. Curr. Protoc. Nucleic Acid Chem. (2010); 40:9.5.1-9.5.23) or through a commercial vendor (e.g., the Aptamer Group). In some embodiments, the small-molecule-binding aptamer binds to the small molecule with a dissociation constant ($K_D$) of no more than 1 micromolar, e.g., no more than 500 nanomolar, no more than 400 nanomolar, no more than 300 nanomolar, no more than 200 nanomolar or no more than 100 nanomolar.

In some embodiments, the small-molecule-binding aptamer is a theophylline-binding aptamer or 3-methylxanthine-binding aptamer, optionally wherein the aptamer binds to theophylline or 3-methylxanthine, respectively, with a dissociation constant ($K_D$) of no more than 1 micromolar, e.g., no more than 500 nanomolar, no more than 400 nanomolar, no more than 300 nanomolar, no more than 200 nanomolar or no more than 100 nanomolar. In some embodiments, the small-molecule-binding aptamer is a theophylline-binding aptamer, a 3-methylxanthine-binding aptamer or a anhydrotetracycline-binding aptamer, optionally wherein the aptamer binds to theophylline, 3-methylxanthine or anhydrotetracycline, respectively, with a dissociation constant ($K_D$) of no more than 1 micromolar, e.g., no more than 500 nanomolar, no more than 400 nanomolar, no more than 300 nanomolar, no more than 200 nanomolar or no more than 100 nanomolar. The structures of theophylline, 3-methylxanthine, and anhydrotetracycline are shown below.

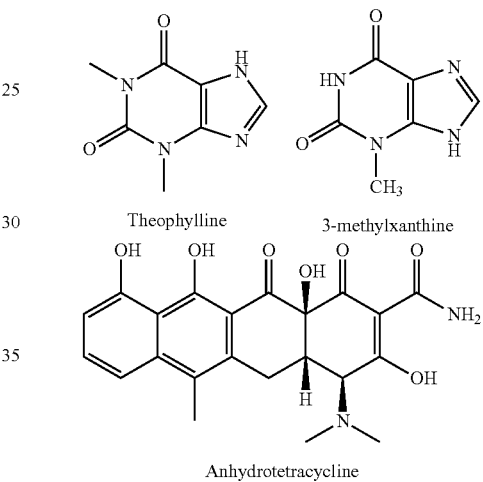

Theophylline   3-methylxanthine

Anhydrotetracycline

In some embodiments, the small-molecule-binding aptamer is a theophylline-binding aptamer and the theophylline-binding aptamer comprises the sequence 5'-AUACCAGCUUCGAAAGAAGCCCUUGGCAG-3' (SEQ ID NO: 95), optionally with up to 5, 4, 3, 2 or 1 substitutions, deletions, or additions. In some embodiments, the small-molecule-binding aptamer is a 3-methylxanthine-binding aptamer and the 3-methylxanthine-binding aptamer comprises the sequence 5'-AUACCAGCUUCGAAAGAAGCCAUUGGCAG-3' (SEQ ID NO: 96), optionally with up to 5, 4, 3, 2 or 1 substitutions, deletions, or additions. In some embodiments, the small-molecule-binding aptamer is an anhydrotetracycline-binding aptamer and the anhydrotetracycline-binding aptamer comprises the sequence 5'-GAGAGGUGAAGAAUACGACCACCUAG-GUAGAAAUACCUAAAACAUAC-3'(SEQ ID NO: 180), optionally with up to 5, 4, 3, 2 or 1 substitutions, deletions, or additions.

Ribonucleoproteins

Other aspects of the disclosure relate to a ribonucleoprotein (RNP) comprising an sgRNA, e.g., an sgRNA as described herein, and an RNA-guided endonuclease, such as a Cas enzyme. In some embodiments, the RNP may be expressed in or introduced into a bacterium. In some embodiments, a composition is provided that comprises an RNP, e.g., an RNP as described herein.

The RNA-guided endonuclease can be any RNA-guided endonuclease known in the art or described herein. In some embodiments, the RNA-guided endonuclease is a CRISPR class 2 type II Cas enzyme, including variants and homologs thereof. In some embodiments, the RNA-guided endonuclease is a Cas9 enzyme, including variants and homologs thereof. Examples Cas9 enzymes include S. pyogenes Cas9 (SpCas9), S. aureus Cas9 (SaCas9), S. thermophilus Cas9 (StCas9), F. novicida Cas9 (FnCas9), N. meningitidis Cas9 (NmCas9), and B. laterosporus Cas9 (BlatCas9), as well as variant forms of such enzymes (see, e.g., Nakade et al. Cas9, Cpf1 and C2c1/2/3—What's next? Bioengineered. 2017; 8(3): 265-273 and Komor et al. CRISPR-based technologies for the manipulation of eukaryotic genomes. Cell. 2017; 168(1-2): 20-36). PAM sequences corresponding to such enzymes are known in the art. Example PAM sequences for such enzymes include NRG, NGG, NGAG, NGCG, NGRRT, NGRRN, NNNNGATT, and NNAGAAW (see, e.g., Nakade et al. Cas9, Cpf1 and C2c1/2/3—What's next? Bioengineered. 2017; 8(3): 265-273 and International Patent Application Publication No. WO2016196805). In some embodiments, the Cas9 enzyme has at least 90% identity with (e.g., at least 91%, at least 92%, at least 93%, at least 94%, at least 95%, at least 96%, at least 97%, at least 98%, or at least 99% identity with) or comprises the following amino acid sequence (SEQ ID NO: 179):

```
MDKKYSIGLDIGTNSVGWAVITDEYKVPSKKFKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLFGNLIALS

LGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIE

KILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLK

TYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKK

GILQTVKVVDELVKVMGRHKPENIVIEMARENQTTQKGQKNSRERMKRI

EEGIKELGSQILKEHPVENTQLQNEKLYLYYLQNGRDMYVDQELDINRL

SDYDVDHIVPQSFLKDDSIDNKVLTRSDKNRGKSDNVPSEEVVKKMKNY

WRQLLNAKLITQRKFDNLTKAERGGLSELDKAGFIKRQLVETRQITKHV

AQILDSRMNTKYDENDKLIREVKVITLKSKLVSDFRKDFQFYKVREINN

YHHAHDAYLNAVVGTALIKKYPKLESEFVYGDYKVYDVRKMIAKSEQEI

GKATAKYFFYSNIMNFEKTEITLANGEIRKRPLIETNGETGEIVWDKGR

DFATVRKVLSMPQVNIVKKTEVQTGGFSKESILPKRNSDKLIARKKDWD

PKKYGGFDSPTVAYSVLVVAKVEKGKSKKLKSVKELLGITIMERSSFEK

NPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQIS

EFSKRVILADANLDKVLSAYNKHRDKPIREQAENIIHLFTLTNLGAPAA

FKYFDTTIDRKRYTSTKEVLDATLIHQSITGLYETRIDLSQLGGD
```

Methods of Inducing Gene Editing

Yet other aspects of the disclosure relate to a method of inducing gene editing in a bacterium. As used herein, "inducing" includes both (a) causing a bacterium in which no editing is occurring to become a bacterium in which gene editing occurs to some extent and (b) increasing, in a bacterium in which at least some editing is occurring, the level of editing occurring (e.g., increasing the editing efficiency in a given bacterium from 1% editing efficiency to 50% editing efficiency). In both (a) and (b), the extent to which gene editing is occurring is increased (in (a), from 0 to some and in (b), from some to more).

In some embodiments, the method comprises (a) introducing or expressing an sgRNA, e.g., an sgRNA as described herein (e.g., comprising a small-molecule-binding aptamer sequence adjacent to a region comprising a 2×4 internal loop and upper stem), in a bacterium, (b) introducing or expressing a Cas enzyme, e.g., a Cas enzyme as described herein (e.g., a Cas9 enzyme), in the bacterium, and (c) contacting the bacterium with a small molecule, e.g., a small molecule as described herein, that interacts with the aptamer sequence, e.g., an aptamer sequence as described herein (e.g., small-molecule-binding aptamer sequence), in the sgRNA such that gene editing is induced in the bacterium. In some embodiments, step (c) is performed after steps (a) and (b), e.g., at least 5 minutes, at least 10 minutes, at least 20 minutes, at least 30 minutes, at least 50 minutes, at least 1 hour, at least 2 hours, at least 4 hours, at least 8 hours, at least 12 hours, at least 24 hours after steps (a) and (b). In some embodiments, steps (a) and (b) are performed sequentially. In some embodiments, steps (a) and (b) are performed at the same time. In some embodiments, steps (a), (b) and (c) are performed at the same time.

Each of the sgRNA and the Cas enzyme independently may either be introduced, e.g., by permeabilizing the cell, or may be expressed, e.g., in using a plasmid or other vector that is present in the bacterium. In some embodiments, both the sgRNA and Cas enzymes are expressed, e.g., in using a plasmid or other vector that is present in the bacterium. Example plasmids for expressing a Cas enzyme and an sgRNA are described in the Examples.

The small molecule can be any small molecule described herein. In some embodiments, the small molecule is theophylline or 3-methylxanthine. In some embodiments, the small molecule is contacted with the bacterium at a concentration of at least 0.001 mM, at least 0.01 mM, at least 0.1 mM, at least 1 mM, at least 10 mM or at least 100 mM or more. In some embodiments, the small molecule is contacted with the bacterium at a concentration of between 0.001 mM to 100 mM, e.g., 1 mM.

In some embodiments, the method comprises introducing at least two sgRNAs into the bacterium, wherein a first sgRNA comprises a first small-molecule-binding aptamer sequence, e.g., a small-molecule-binding aptamer sequence as described herein, and a second sgRNA comprises a second small-molecule-binding aptamer sequence, e.g., a small-molecule-binding aptamer sequence as described herein, that is different than the first small-molecule-binding aptamer sequence. In some embodiments, the first sgRNA targets a different region in the bacterial genome for editing than the second sgRNA (e.g., the first sgRNA and the second sgRNA contain different protospacer sequences in the crRNA region). In some embodiments of this method, the method further comprises contacting the bacterium with a first small molecule that interacts with the first small-molecule-binding aptamer sequence and contacting the bacterium with a second small molecule that interacts with the second small-molecule-binding aptamer sequence. In some embodiments, the first small molecule is theophylline and the second small molecule is 3-methylxanthine. The first small molecule and second small molecule may be contacted with the bacterium at different times or at the same time. In some embodiments, the bacterium is contacted with the first small molecule prior to the second small molecule. In some embodiments, the bacterium is contacted with the second small molecule prior to the first small molecule. In some embodiments, the time between contact with the first small molecule and second small molecule is at least 1 hour, at least 2 hours, at least 3 hours, at least 4 hours, or more. In some embodiments, the time between contact with the first small molecule and second small molecule is between 1 to 10 hours, 1 to 5 hours, 1 to 3 hours, 2 to 10 hours, 3 to 10 hours, 2 to 5 hours, or 3 to 5 hours. In some embodiments, having a time delay between contact with the first small molecule and the second small molecule allows for sequential editing, which may result in improved editing efficiency.

The bacterium used in the method may be any bacterium known in the art or described herein. In some embodiments, the bacterium is a Gram-negative bacterium. In some embodiments, the bacterium is an *E. coli* bacterium.

Methods of Selection

Other aspects of the disclosure relate to methods for selecting one or more switchable aptamer single guide RNAs (agRNAs) that are inducible with a small molecule and/or screening candidate agRNAs. As described herein, in some embodiments, a sgRNA containing an aptamer may need to be optimized or screened for desired inducibility with a small molecule. In some embodiments, the region comprising the 2×4 internal loop and/or upper stem of a sgRNA may need to be optimized or screened such that the aptamer adjacent to the region has a desired inducibility with a small molecule.

As described herein, agRNAs can be selected by a multi-step process. In some embodiments, the method comprises a negative selection step to eliminate candidate agRNAs that are constitutively active followed by a positive selection step to select candidate agRNAs that can be induced with the small molecule to edit a location in the genome. In some embodiments, the negative selection step involves growing the bacteria under conditions such that constitutively active agRNAs will induce double-stranded breaks, which will cause cell death. An example of such conditions includes growing the bacteria in the absence of the small molecule and in the absence of λ-red proteins, which normally increase the frequency of homologous repair of the double-stranded breaks. Candidate agRNAs that do not induce cell death are then subjected to the positive selection step. In some embodiments, the positive selection step involves growing the bacteria under conditions such that bacteria containing inducible agRNAs can be positively identified, e.g., using a selection marker that is identifiable in bacteria containing inducible agRNAs. An example of such conditions includes using galK selection, where an agRNA that is inducible facilitates the introduction of a stop codon into the galK gene such that a bacterium containing the mutated galK gene will survive incubation with 2-deoxygalactose because such bacterium will not metabolize 2-deoxygalactose. In other embodiments, the negative selection step may comprise a galK selection step that comprises growing the bacteria in the absence of the small molecule and in the presence of λ-red protein. Active agRNAs will introduce a stop codon into the galK gene and the selection is carried out in a minimal media that contains galactose as the only carbon source, such that only bacteria containing inactive agRNAs will have a functional galK gene and will survive in the minimal media. The surviving bacteria may then be subjected to the positive selection step. In some embodiments, the negative selection comprises cell death by dsDNA cleavage in the absence of λ-red proteins and the positive selection step comprises survival by introducing a survival-conferring mutation through homologous recombination assisted by λ-red proteins.

In some embodiments, the method comprises (a) performing a negative selection step comprising growing a first plurality of bacteria in the absence of the small molecule and in the absence of λ-red protein expression, thereby inducing cell death in a subset of the plurality to produce a second plurality of bacteria, wherein individual bacteria in the first plurality comprise (i) a nucleic acid encoding a candidate agRNA that produces a cut site in the gene encoding a selection marker protein, (ii) a Cas enzyme (e.g., Cas9), and (iii) a template for homologous repair of the cut site in the gene that encodes the selection marker protein; (b) performing a positive selection step comprising either (i) growing the second plurality of bacteria in the presence of the small molecule and λ-red protein expression; or (ii) isolating nucleic acids encoding candidate agRNAs from the second plurality of bacteria and introducing the nucleic acids into a third plurality of bacteria and growing the third plurality of bacteria in the presence of the small molecule and λ-red protein expression, wherein individual bacteria in the third plurality comprise (i) a nucleic acid encoding a candidate agRNA that produces a cut site in the gene encoding a selection marker protein, (ii) a Cas enzyme, and (iii) a template for homologous repair of the cut site in the gene that encodes the selection marker protein; and (c) selecting at least one bacterium from step (b) that expresses the altered selection marker protein. In some embodiments, the steps of the method may be iterated, e.g., steps (a), (b) and/or (c) may be repeated once, twice, three times, four times, or more.

In other embodiments, the method comprises (a) performing a negative selection step comprising growing a first plurality of bacteria in the absence of the small molecule and in the presence of λ-red protein expression, thereby inducing cell death in a subset of the plurality to produce a second plurality of bacteria, wherein individual bacteria in the first plurality comprise (i) a nucleic acid encoding a candidate agRNA that produces a cut site in the gene encoding a selection marker protein, (ii) a Cas enzyme (e.g., Cas9), and (iii) a template for homologous repair of the cut site in the gene that encodes the selection marker protein; (b) performing a positive selection step comprising either (i) growing the second plurality of bacteria in the presence of the small molecule and λ-red protein expression; or (ii) isolating nucleic acids encoding candidate agRNAs from the second plurality of bacteria and introducing the nucleic acids into a third plurality of bacteria and growing the third plurality of bacteria in the presence of the small molecule and λ-red protein expression, wherein individual bacteria in the third plurality comprise (i) a nucleic acid encoding a candidate agRNA that produces a cut site in the gene encoding a selection marker protein, (ii) a Cas enzyme, and (iii) a template for homologous repair of the cut site in the gene that encodes the selection marker protein; and (c) selecting at least one bacterium from step (b) that expresses the altered selection marker protein. In some embodiments, the steps of the method may be iterated, e.g., steps (a), (b) and/or (c) may be repeated once, twice, three times, four times, or more.

In some embodiments, the candidate agRNA(s) is/are sgRNA(s), e.g., sgRNA(s) as described herein, e.g., comprising a small-molecule-binding aptamer sequence adjacent to a region comprising a 2×4 internal loop and upper stem. In some embodiments, the nucleic acid encoding the candidate agRNA is a plasmid. In some embodiments, the template for homologous repair is contained within a plasmid. In some embodiments, the nucleic acid encoding the candidate agRNA and the template for homologous repair are contained within the same plasmid. In some embodiments, bacteria in the first and/or second and/or third plurality comprise a plasmid that encodes a Cas enzyme (e.g., Cas9) and a plasmid that encodes a λ-red protein. In some embodiments, bacteria in the first and/or second and/or third plurality comprise a plasmid that encodes a Cas enzyme (e.g., Cas9) and that encodes a λ-red protein. Example plasmids that encode Cas9 and λ-red protein include X2-Cas9 (Addgene plasmid number #85811) and pSIM5 (see, e.g., Datta et al. A set of recombineering plasmids for gram-negative bacteria. Gene. (2006); 379, 109-115).

The selection marker protein can be any selection marker protein that allows for positive identification of inducible agRNAs. In some embodiments, the selection marker protein is an antibiotic resistance protein, a metabolic protein that enable survival in a defined media or an engineered kill-switch. In some embodiments, the selection marker protein is galK and the template for homologous repair comprises a premature stop codon for the galK gene. In some embodiments, when the selection marker protein is galK, then step (a) of the method is performed in a minimal media that contains galactose as the only carbon source. In some embodiments, when the selection marker protein is galK, then step (B) of the method is performed in a media comprising 2-deoxygalactose. In some embodiments, the selection marker protein is two proteins, e.g., a tetA protein and a sacB protein (see, e.g., Li et al. Positive and negative selection using the tetA-sacB cassette: recombineering and P1 transduction in *Escherichia coli*, Nucleic Acids Res. 2013 December; 41(22):e204).

The small molecule can be any small molecule described herein. In some embodiments, the small molecule is theophylline or 3-methylxanthine. In some embodiments, the small molecule is contacted with the plurality of bacteria at a concentration of at least 0.1 mM, at least 1 mM, at least 10 mM or at least 100 mM or more. In some embodiments, the small molecule is contacted with the plurality of bacteria at a concentration of between 0.1 mM to 100 mM, e.g., 1 mM.

In some embodiments, the first and/or second and/or third plurality of bacteria comprises at least $10^1$, at least $10^2$, at least $10^3$, at least $10^4$, at least $10^5$, at least $10^6$, at least $10^7$, at least $10^8$, at least $10^9$, or at least $10^{10}$ bacteria. The bacteria used in the method may be any bacteria known in the art or described herein. In some embodiments, the bacteria is gram-negative bacteria. In some embodiments, the bacteria is *E. coli* bacteria.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

CRISPR-Cas9 has led to great advances in gene editing for a broad spectrum of applications. To further the utility of Cas9, there have been efforts to achieve temporal control over its nuclease activity. While different approaches have focused on regulation of Cas9 or gRNA-regulated CRISPR interference, none of the reported methods enable stringent control of the nuclease activity in an orthogonal and multiplexed manner. Here, novel RNA linkers were developed to combine theophylline- and 3-methylxanthine (3MX)-binding aptamers with the gRNA, enabling small molecule-dependent editing in *Escherichia coli*. These activatable guide RNAs enable orthogonal, temporal and post-transcriptional control of in vivo gene editing. Further, they reduce the death of host cells caused by cuts in the genome, a major limitation of CRISPR-mediated bacterial recombineering. Temporal control of the enzyme will simultaneously increase library coverage and decrease bias in multiplex CRISPR/Cas9 editing experiments.

Figure 4A:
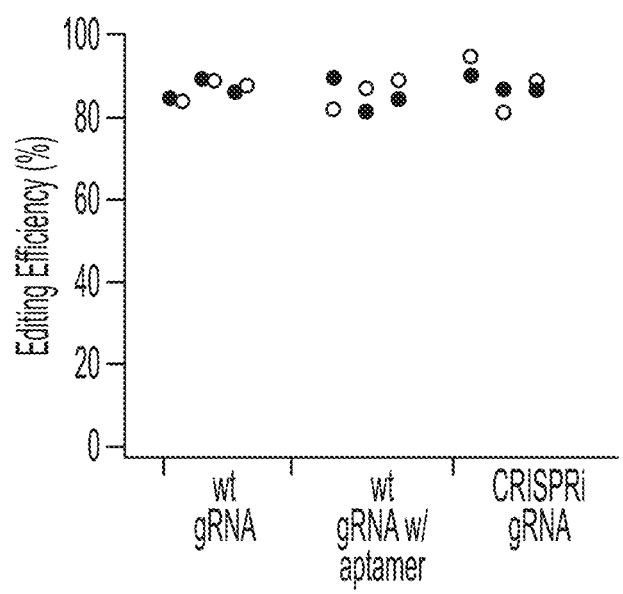
FIGS. 4A-4B show the editing efficiencies at the galK 1 site.
Figure 4B:
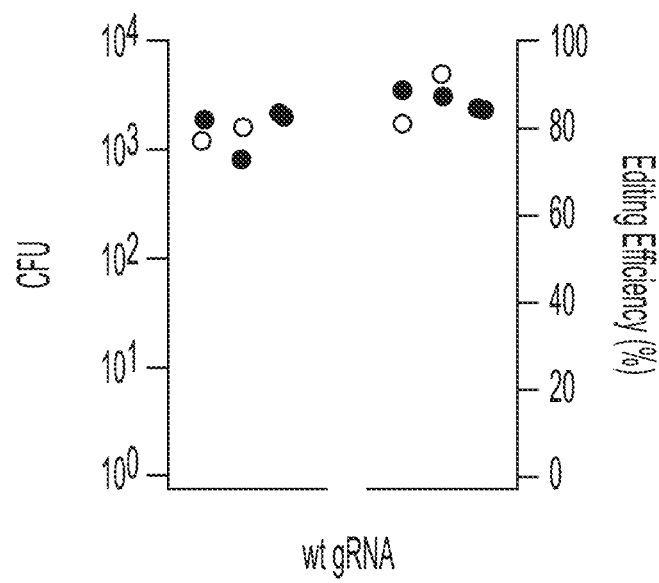

The utility of CRISPR for genome editing in *E. coli* has been demonstrated in various studies. One of those newly developed methods, called CREATE, uses plasmid-based recombineering, as opposed to the use of oligos, which enables easy tracking of the mutations in a library. However, CREATE, like other CRISPR-based editing technologies, suffers from low transformation efficiencies caused by the lethality of dsDNA breaks in bacteria and from associated issues, such as biases in multiplexed libraries towards non-cutting gRNAs. For this reason, inducible gRNAs were developed that would allow timing and titration of the nuclease activity to alleviate these issues. Previously, inducible gRNAs were developed for CRISPRi applications but could not be applied for inducible gene editing (FIG. 4A) due to the associated "leakiness"—the same reason why inducible promoters could not be used to solve the problem (FIG. 4A).

Figure 1B:
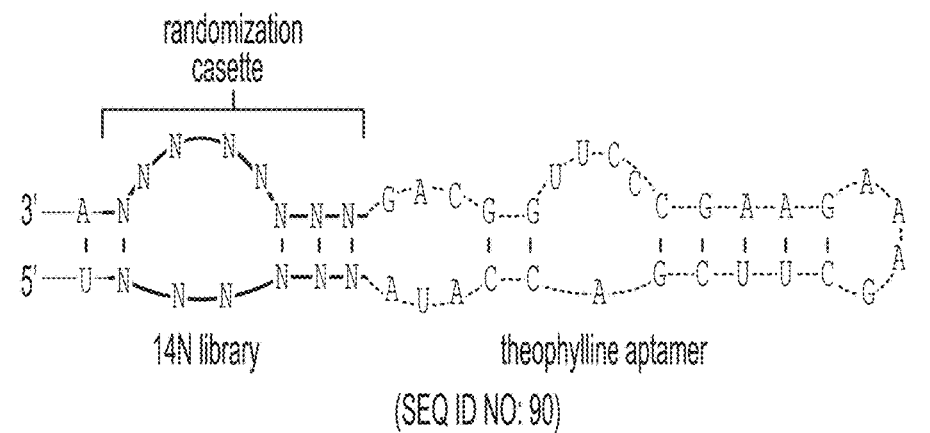
Figure 1B:
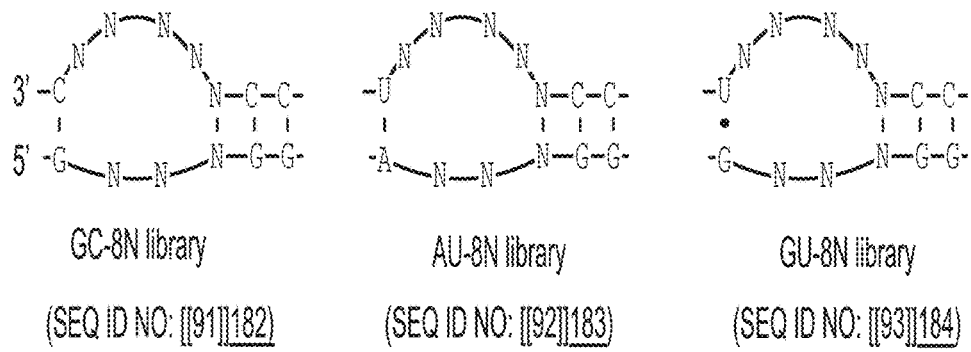

CREATE technology was used as a platform to develop ligand-switchable sgRNAs to reduce the DNA damage stress on the host bacteria. As a first step, the tetraloop used to fuse the crRNA and tracrRNA[16] (FIG. 1A) was replaced with an in vitro selected small molecule binding aptamer (FIG. 1A). This site is highly tolerant of insertions[17] and a theophylline aptamer-sgRNA fusion with an unchanged internal loop (IL) is constitutively active (FIG. 4A). To generate switchable aptamer-sgRNAs or "agRNAs", a region including the IL and a small helix (upper stem) that connects the aptamer with the sgRNA was randomized. Nucleotides in the IL are critical for nuclease activity[18] and directly interact with the PAM-interacting (PI) domain of Cas9[19]. Without wishing to be bound by theory, it is hypothesized that specific sequences could communicate ligand-dependent conformational changes in the aptamer to Cas9 to regulate nuclease activity (FIG. 1).

Figure 1C:
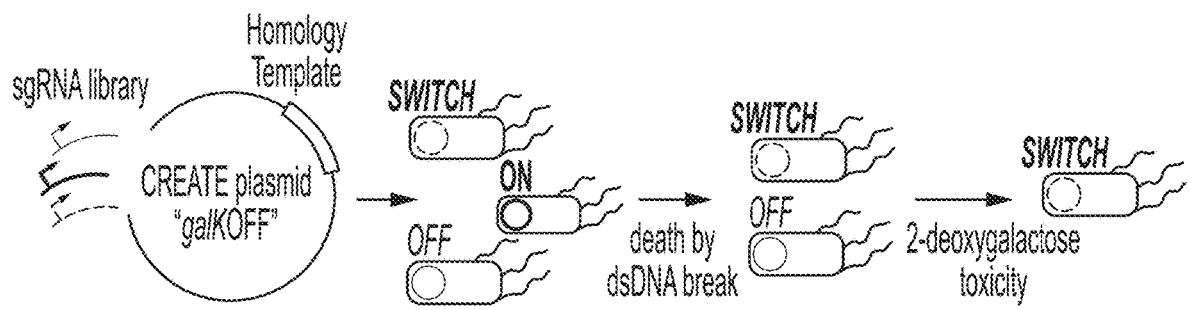
Figure 1D:
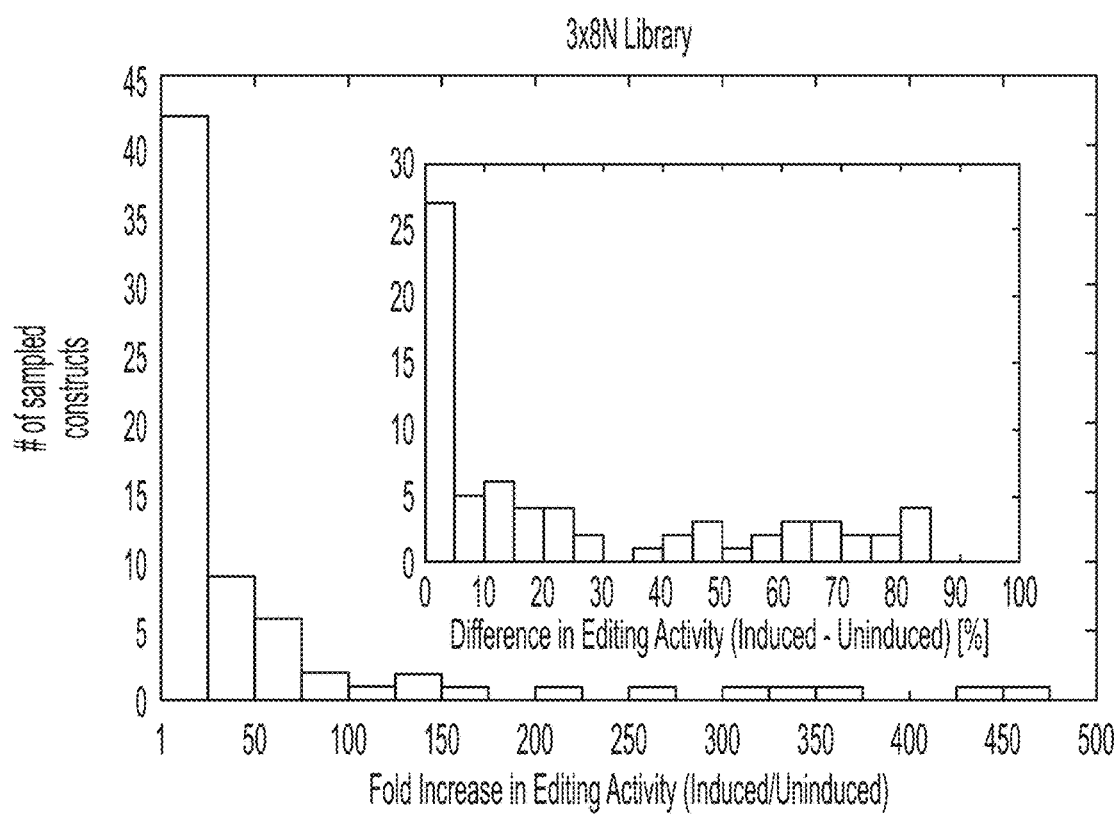

A fully randomized 14 nucleotide (14N) library was subjected to an in vivo survival assay in *E. coli*. Each agRNA of the library was cloned into a plasmid vector constitutively expressing the agRNA and containing the template for homologous repair of the cut site targeted by the agRNA. The cloned plasmid library was transformed into *E. coli* MG1655 to enrich theophylline-dependent agRNAs using a galK selection assay[20] in liquid culture. The MG1655 strain used for the selection also carries the pSIM521 plasmid which expresses the λ-red proteins from a heat-inducible promoter and pX2-Cas922 which expresses Cas9 from the arabinose-inducible pBAD promoter. This strain will be referred to as MGλ9. In the first selection step MGλ9 was transformed with the agRNA library but theophylline was not added to the recovery media so switchable agRNAs in the library would be inactive. This step was performed without inducing expression of the λ-red proteins but with induced Cas9 expression so constitutively active agRNAs that target the galK1 site in the galK gene generate a double-stranded DNA break leading to cell death, eliminating constitutively active agRNA constructs from the selection (FIG. 1C). The second selection step was facilitated by the Cas9-mediated recombineering technology CREATE®. First, the MGλ9 strain was transformed with the recovered plasmid library from the first step and theophylline was added to the recovery media to induce switchable agRNAs. Heat-induced expression of λ-red proteins enabled repair of the DNA break at the site galK1, created by activated agRNAs. Homologous recombination using a template provided on the agRNA plasmid introduced a premature stop codon into the galK gene preventing them from fermenting galactose. Edited cells could then be selected for by growing in minimal media containing the toxic galactose analog 2-deoxygalactose; only recombined bacteria that do not metabolize 2-deoxygalactose survive. Therefore, bacteria expressing activatable agRNAs in the presence of theophylline are enriched in this step (FIG. 1C). These selection/counterselection steps were iterated three times.

Figure 5:
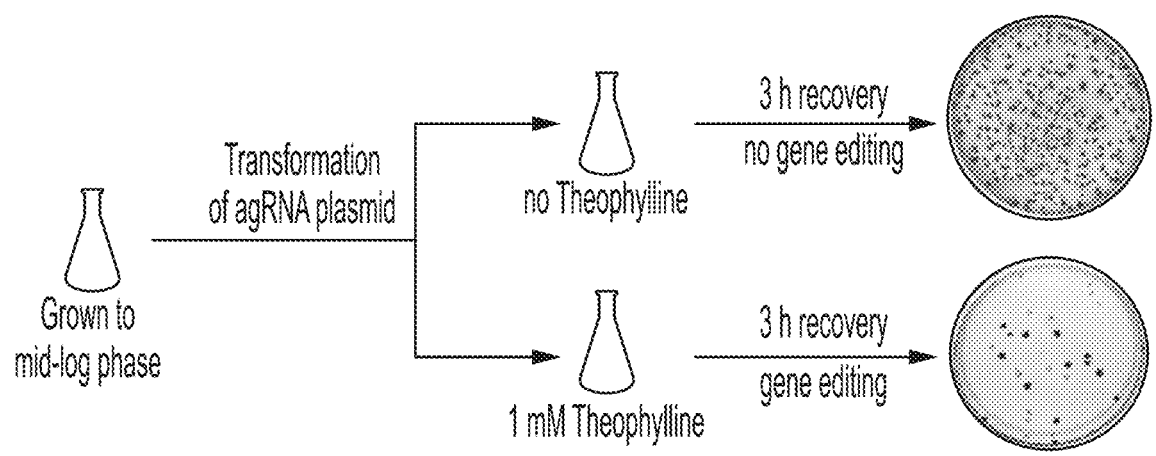
FIG. 5 is a schematic showing the work-flow of the screening process, based on the CREATE protocol. The bacteria were recovered for 3 hours after transformation with the aptamer ligand and then plated on MacConkey agar, containing galactose as the only source of sugar. White colonies were genomically unedited and unable to ferment galactose.

Candidates from this enriched library were analyzed to inform an improved library design. After three selection/counterselection steps, cells were plated on M63 selection medium[20] and 150 colonies were picked. Each isolated candidate was then transformed into unedited *E. coli* to screen for theophylline-responsive constructs using a red/white colony assay to quantify the percentage of edited bacteria. Colonies with an unedited galK site appear red whereas edited colonies appear white (FIG. 5). The percentage of white colonies is considered the editing efficiency. Gene editing was induced as previously described with or without adding theophylline and the editing efficiencies were compared.

Analysis of the 150 colonies from the 14N theophylline agRNA library after the selection yielded 16 theophylline-responsive constructs (Table 3), of which 3 constructs (A1, A9, A14) were found twice. In these sequences, a strong preference for Watson-Crick base pairs was observed in the regions flanking the IL (Table 4). Based upon this insight, more restricted libraries were generated in which three base pairs were fixed, which were predicted to contain a higher percentage of switchable agRNAs within a lower total number of sequences. Three 8N libraries (~6.6×10⁴ sequences) were created that included two G-C pairs in the upper stem and one base pair at the 3'-side of the repeat/antirepeat helix (FIG. 1). Both libraries were transformed in sufficient numbers so as to ensure complete library coverage with 95% confidence[24]. After the galK selection assay was used to enrich switchable constructs from those libraries, 20 colonies were screened from each library. Three sequences (GC7, GC10, GU10) out of the 60 from the three libraries were found twice. The low redundancy among the sequences of the initial and optimized libraries shows that even after enrichment, the screening only covered a fraction of the switchable constructs. The editing efficiencies of the individual constructs from these libraries are displayed in Table 3. Although most screened agRNA constructs were constitutively inactive (FIG. 1D), 13 out of 60 constructs from the restricted theophylline libraries showed a >50-fold increase in editing efficiency (FIG. 1D) as opposed to 5 out of 150 from the initial screen. This demonstrates that the optimization of the library design was successful in increasing the fraction of switchable constructs in the library.

Figure 1E:
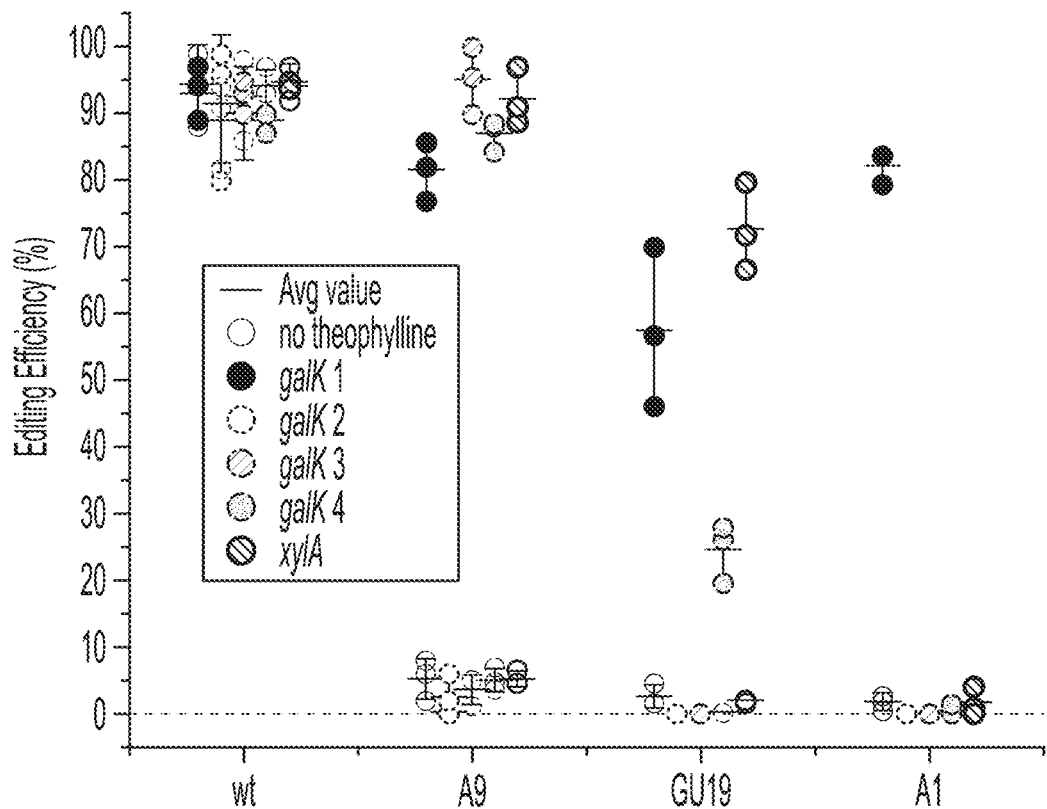
Figure 1E:
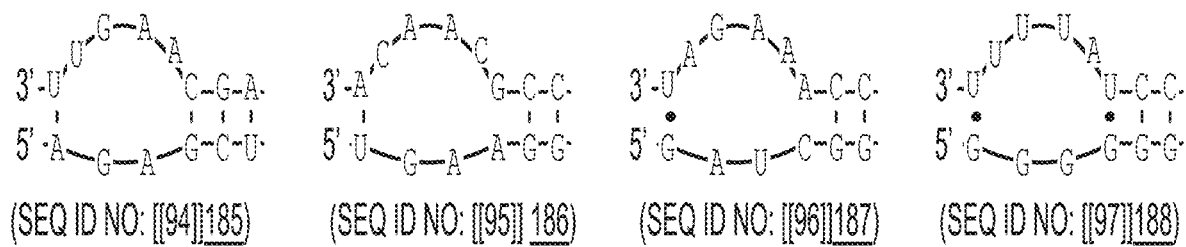
Figure 6:
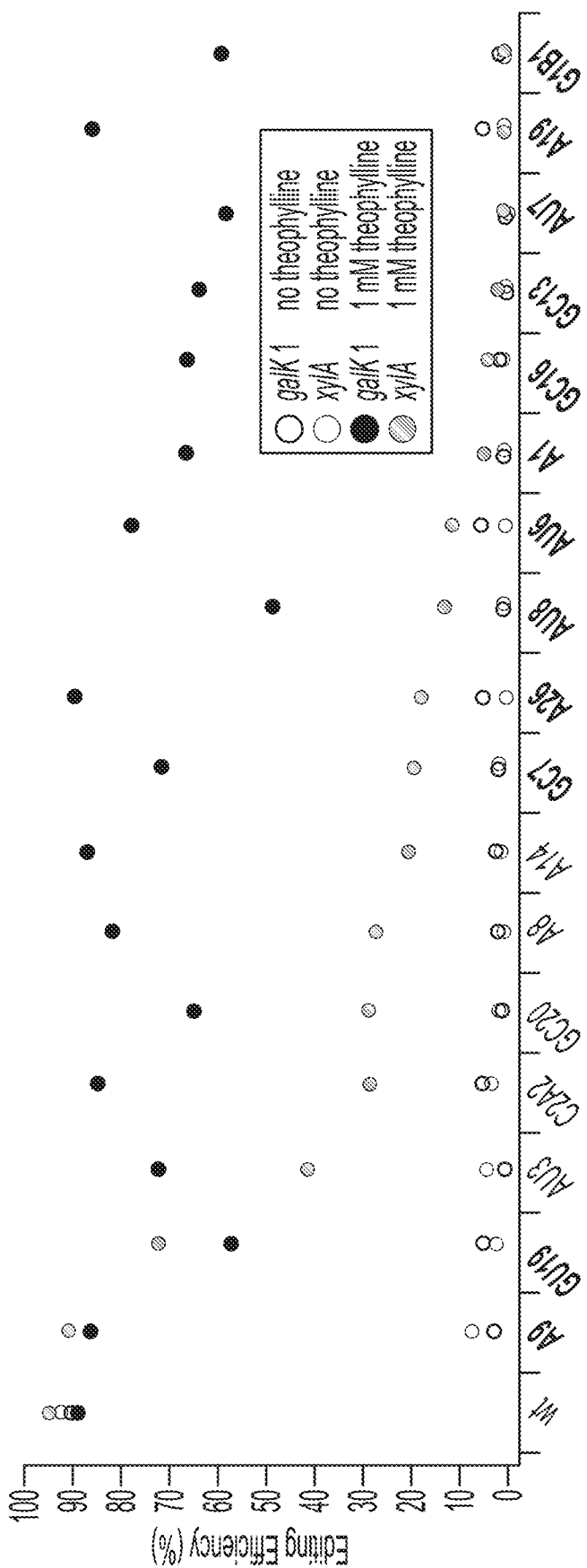
FIG. 6 shows the editing efficiencies of different agRNAs at the galK 1 site and the xylA site. Full circles: 1 mM theophylline. Empty circles: no theophylline.
Figure 7:
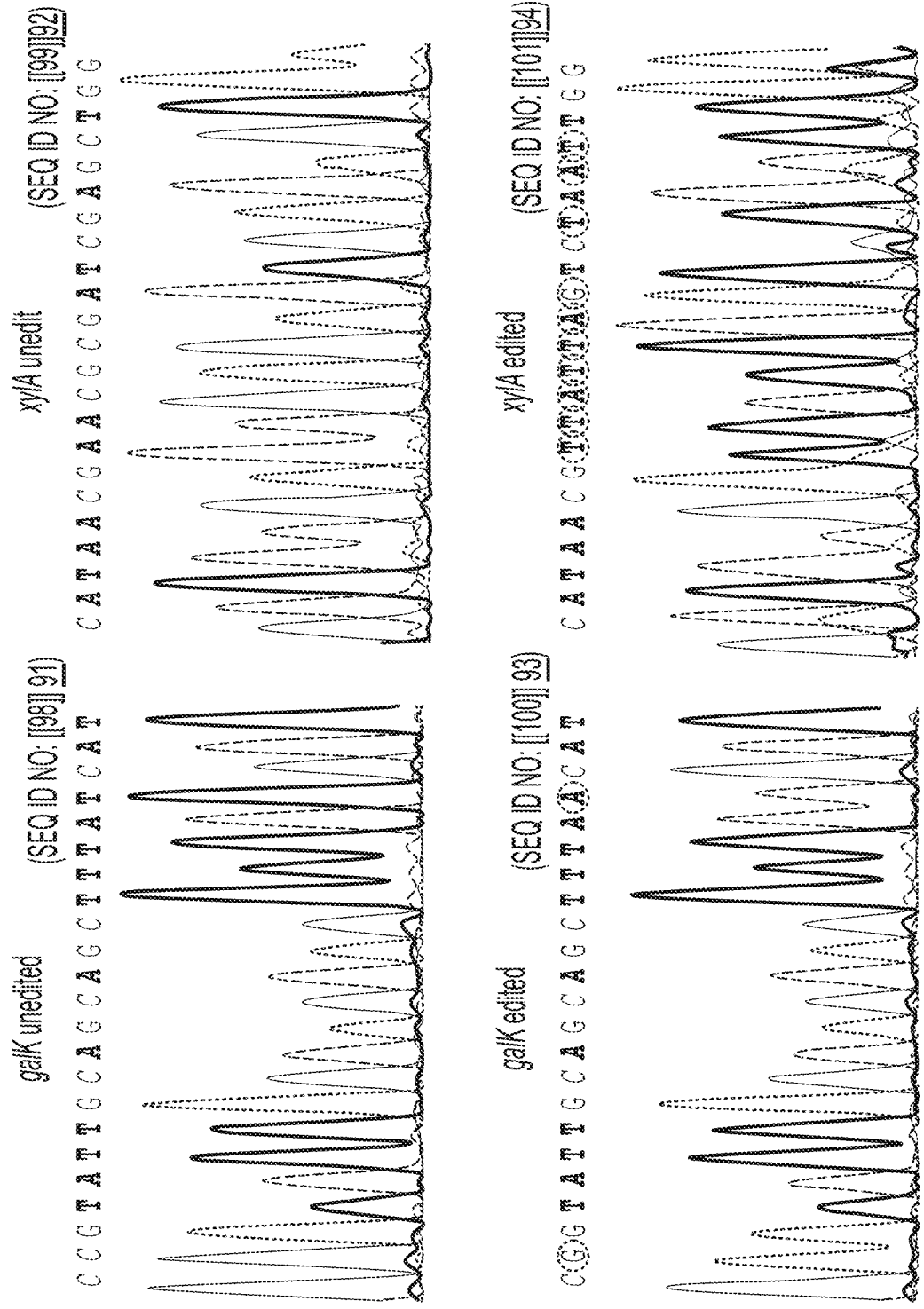
FIG. 7 shows the traces from Sanger sequencing after colony PCR, confirming the genomic edit in colonies with white appearance and showing no edits in colonies with red appearance.

Promising agRNA constructs were analyzed in further detail. 17 agRNA constructs showed a combined >10-fold induction and >40% editing efficiency when induced and were selected for further screening. The xylA gene was targeted with these 17 agRNAs to test whether a different spacer sequence affects the performance. Editing was quantified with the same red/white screen. Two agRNAs (A9 and GU19) showed an editing efficiency at xylA similar to the galK1 site used during selection, while 9 others showed >10% editing at xylA (FIG. 6). To confirm sequence independence of those two agRNAs, they were used to edit three more alternative sites at the galK gene. Only one of those sites was not targetable with agRNA A9; GU19 was more site-dependent, but also showed less background activity (FIG. 1E). Sequencing confirmed that the phenotypic change in the assay corresponded to a designed genomic edit (FIG. 7). The observation that a number of agRNAs only act at the selected galK1 site highlights that the CRISPR-Cas9 system can be selected to act at a single sequence, a feature that could be exploited for reducing off-target effects.

Figure 2A:
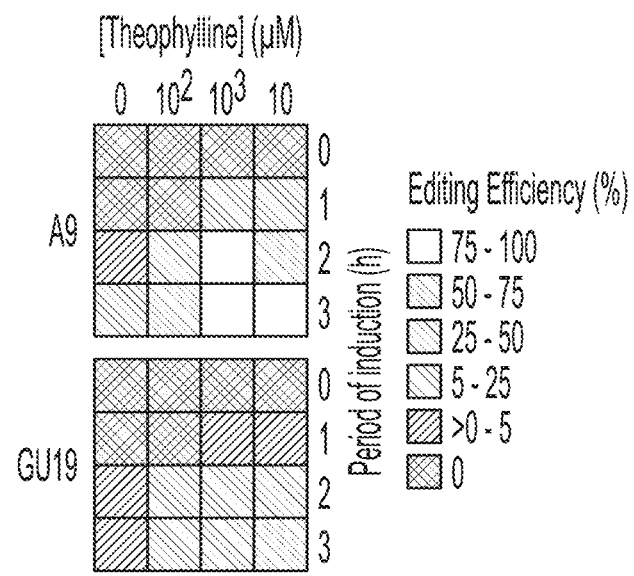
FIGS. 2A-2C show the characterization of selected agRNAs.
Figure 2B:
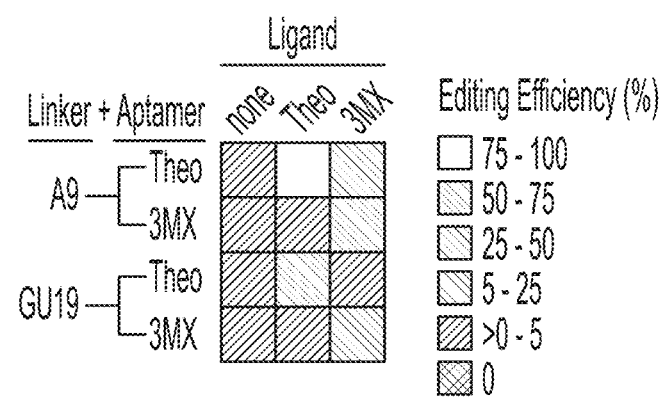
Figure 8:
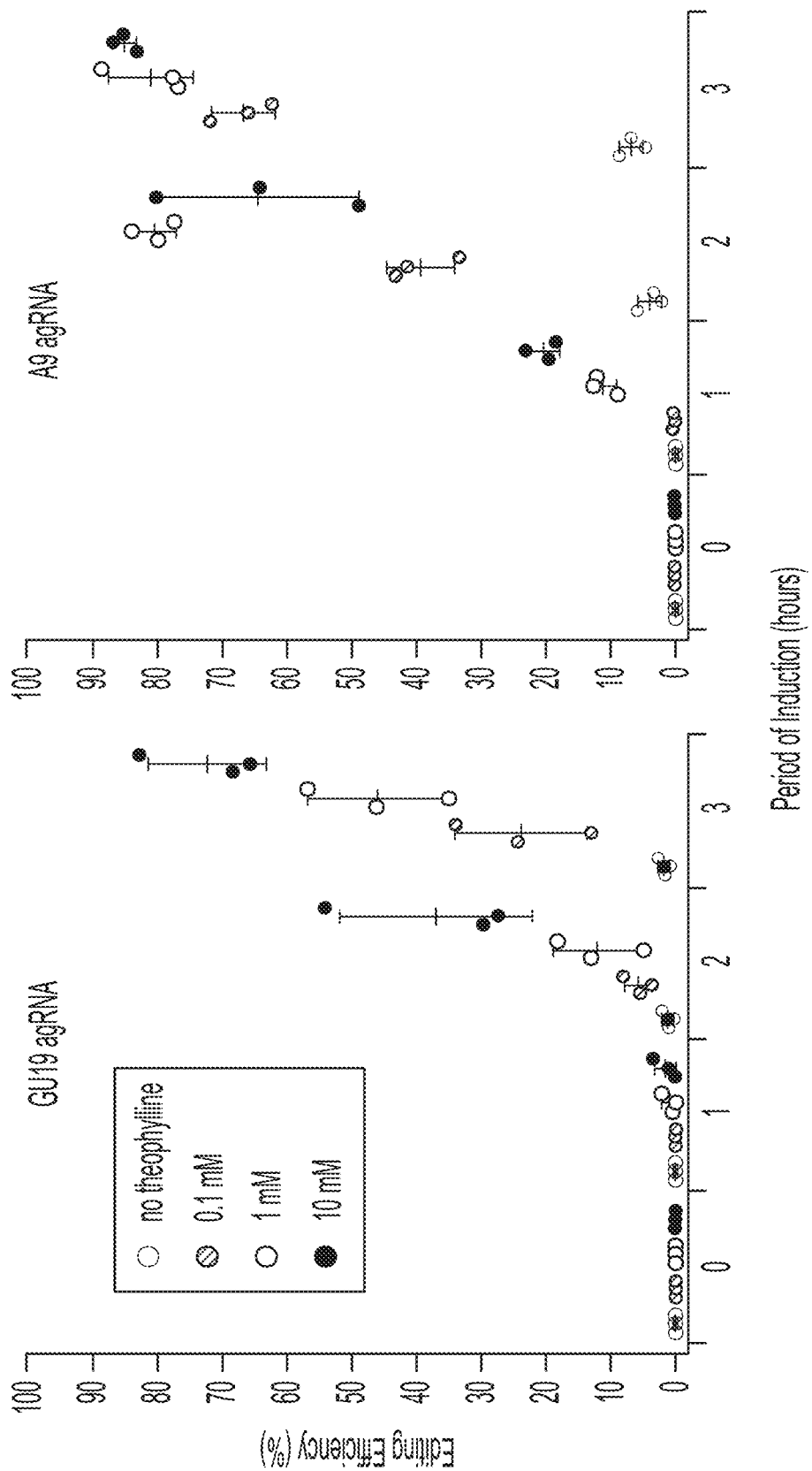
FIG. 8 is a pair of graphs which detail the single data points summarized in FIG. 2A. The underlying data is identical. Error bars indicate +/− standard deviation from the mean.
Figure 9:
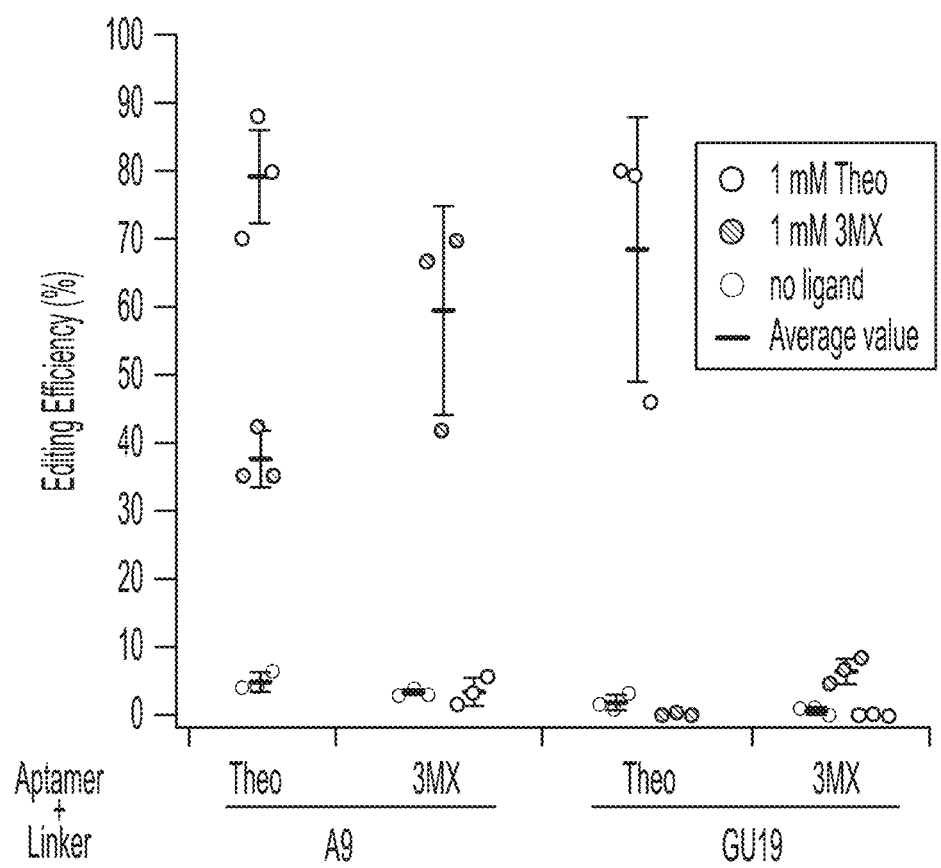
FIG. 9 is a graph which details the single data points summarized in FIG. 2B. The underlying data is identical. Error bars indicate +/− standard deviation from the mean.

To investigate the effect of ligand binding on the gene editing, the concentration and induction time with theophylline was systematically varied. This showed that the editing efficiency increased with the concentration of theophylline and induction time (FIG. 2A, FIG. 8). The concentration of theophylline in the media needed for rapid editing greatly exceeds the $K_D$ of the isolated aptamer (400 nM), an observation typical for synthetic or natural ligand-activatable RNA devices. To test whether the binding of the ligand to the aptamer is the trigger of the agRNA activation, the C22A point mutation was introduced at the ligand-binding site of the theophylline aptamer domain[28]. As expected, this turned the theophylline aptamer into a 3-methylxanthine aptamer, that was not activatable by theophylline (FIG. 2B, FIG. 9). This not only illustrated that ligand recognition by the aptamer is necessary for agRNA activation, it also expands the toolbox by an orthogonal agRNA.

Figure 2C:
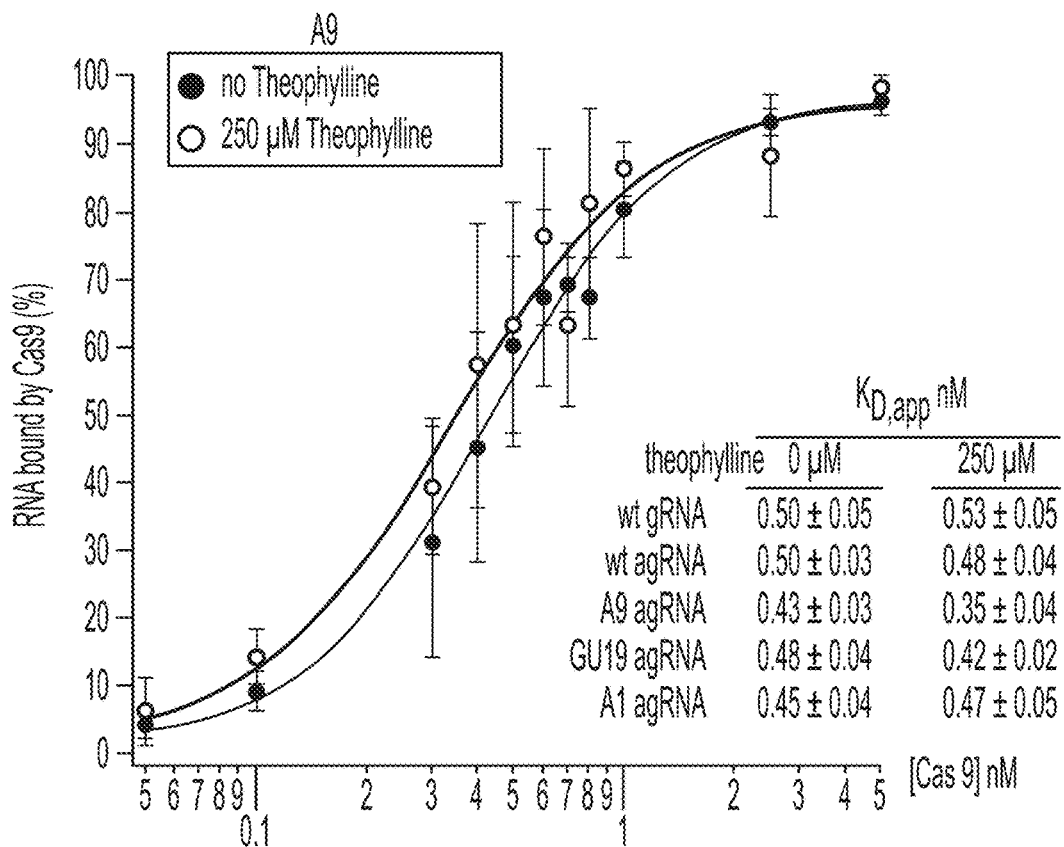
Figure 10:
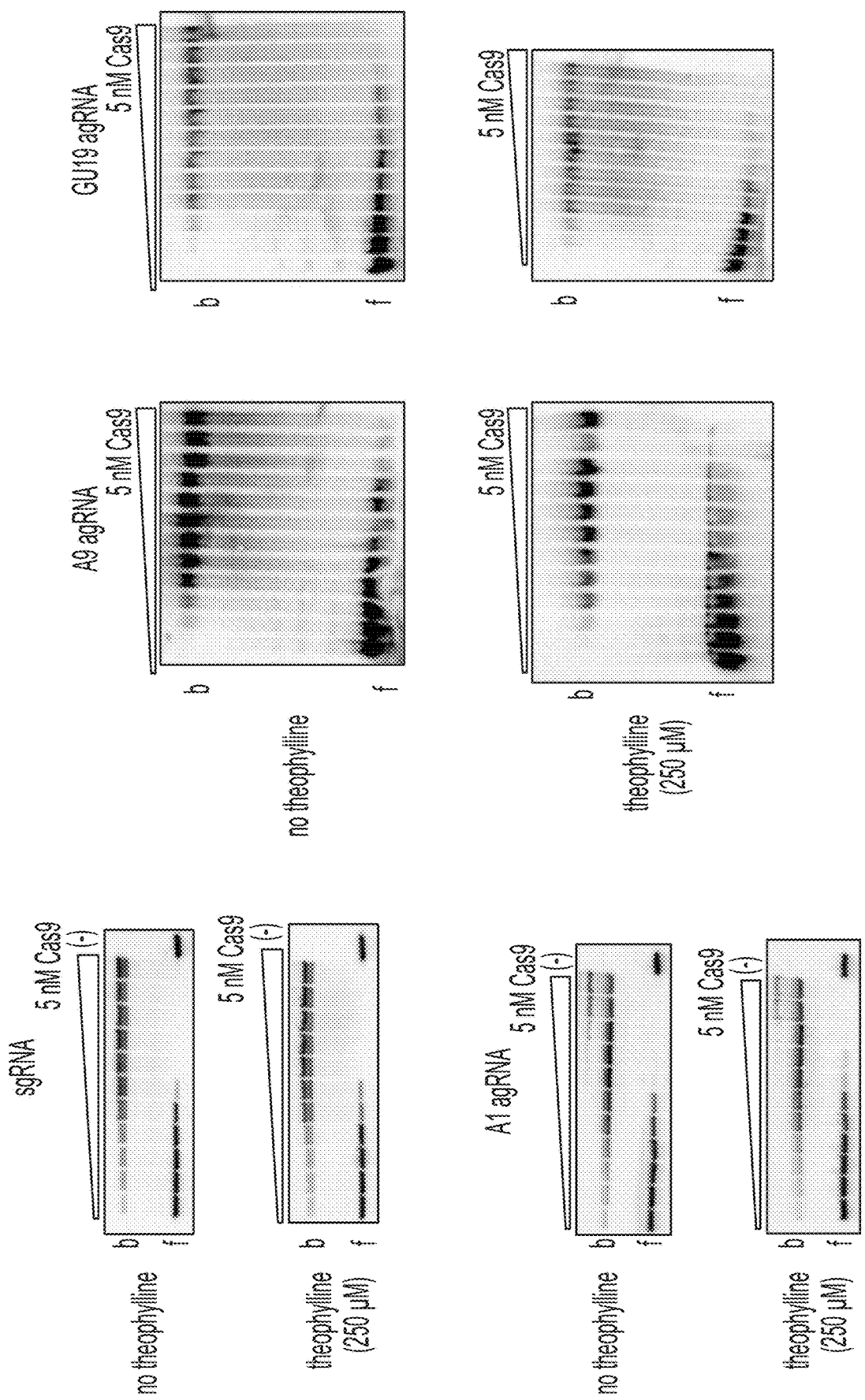
FIG. 10 shows representative images of gels from the electrophoretic mobility shift assay. The upper band corresponds to P32-labeled agRNA bound by Cas9. The lower band corresponds to free P32-labeled agRNA. Images were taken on a Typhoon FLA 9500.

To understand the effects of ligand binding to the aptamer on the activity of Cas9, the binding of the agRNA to the Cas9 protein was investigated. Binding of $^{32}$P-labeled agRNA to Cas9 was quantified using an electrophoretic mobility shift assay (EMSA) (FIG. 10) in the presence or absence of 250 μM theophylline. A1, A9 and GU19 agRNAs all exhibit the same apparent binding affinity to the Cas9 protein as the wild type gRNA, independent of theophylline (FIG. 2C). This indicated that despite the expected disruption of protein-RNA contacts in the randomized region, the RNP assembly is not ligand-dependent. Instead, without wishing to be bound by theory, it is hypothesized that the ligand regulates the recognition and/or cleavage of the DNA target.

Figure 3A:
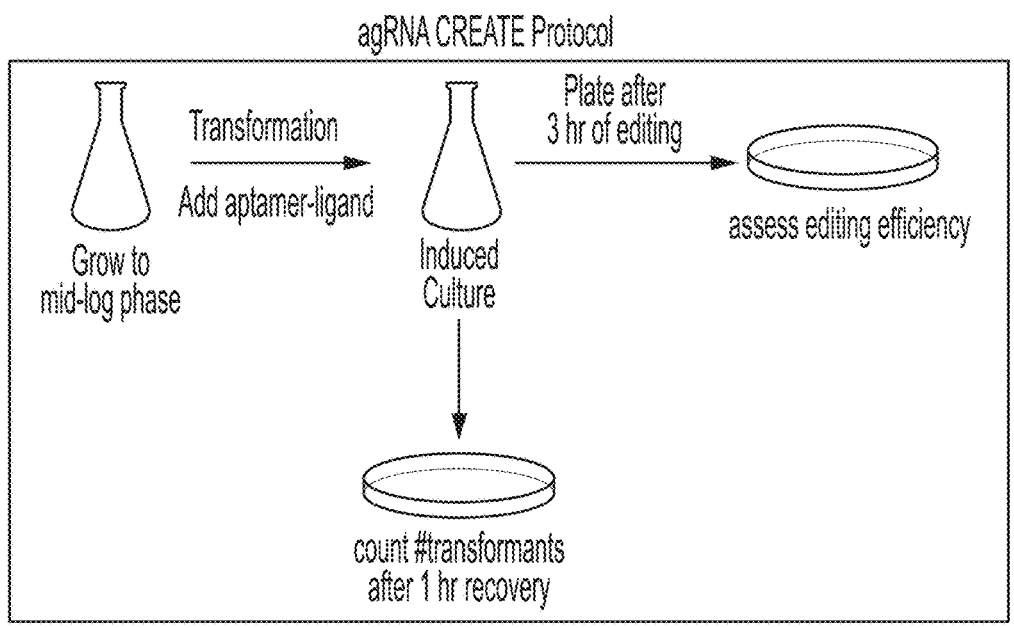
FIGS. 3A-3D show aptamer-gRNAs enable high-throughput genome editing.
Figure 3B:
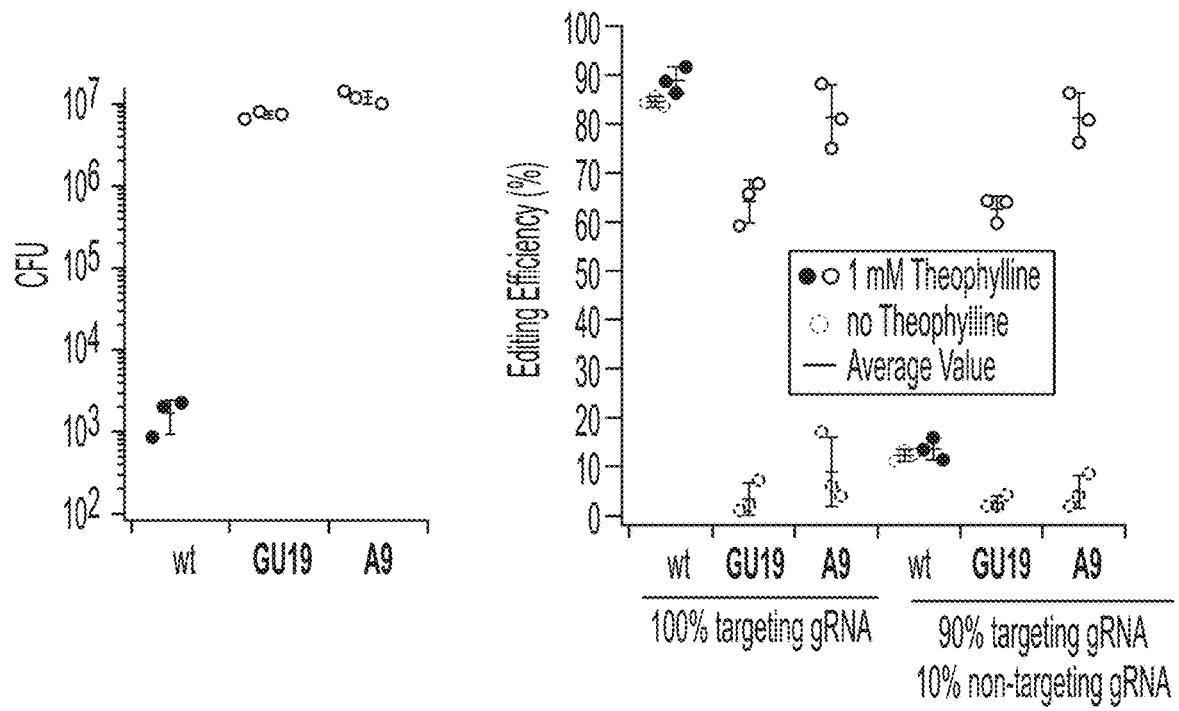

Equipped with temporally controllable agRNAs, the gene editing technology CREATE[10] was optimized. One major drawback of CRISPR-mediated bacterial gene editing technologies is cell death caused by dsDNA cuts[10], despite overexpression of λ-red proteins to increase the frequency of homologous repair. Without wishing to be bound by theory, it is hypothesized that the stress of transformation combined with rapid generation of dsDNA breaks synergistically leads to a high level of cell death. Using the A9 or GU19 agRNAs resulted in a drastic $10^4$-fold increase in number of transformants while maintaining ~80% editing efficiencies (FIG. 3B). Although a low transformation efficiency is not a significant issue when creating a single edit with a defined sgRNA, it dramatically impacts the ability to transform a library of sgRNA plasmids to generate a population of bacteria with different edits. In this process, a portion of gRNAs from the library is expected to be non-functional due to errors in oligonucleotide synthesis, sgRNA misfolding, or inefficient targeting.

Transformants with non-functional gRNAs do not suffer Cas9-mediated DNA cuts and have a strong fitness advantage over transformants with functional gRNAs, resulting in a population dominated by wild type cells. To simulate the transformation of a library containing non-functional gRNAs, bacteria were transformed with a plasmid mixture in which 90% encoded wild type gRNAs that target the galK1 site and are therefore functional and 10% encoded wild type gRNAs that target a site in the eGFP gene, which is absent in this strain, and are therefore non-targeting. Under these conditions, the percentage of edited cells dropped from 89% to 14% (FIG. 3D) and it was sequence-verified that most of the unedited cells carried plasmids expressing non-targeting gRNAs (Table 5). This corresponds to an 8.6±0.1-fold enrichment of the non-targeting plasmids. In contrast, using agRNAs A9 and GU19, the percentage of edited cells was maintained at 81% and 63%, respectively, which shows that non-targeting plasmids were not enriched in the process. This result indicates that separating the stresses caused by transformation and double-stranded breaks can dramatically increase cell survival, hence decreasing the fitness differences between cells harboring functional and non-functional gRNAs.

Figure 3C:
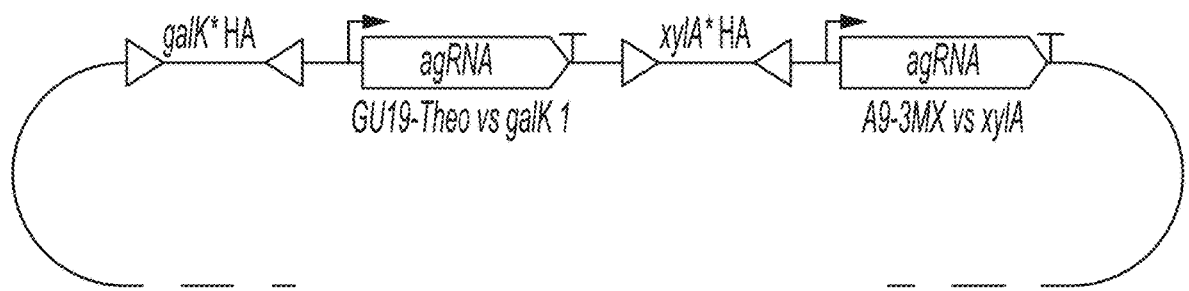
Figure 3D:
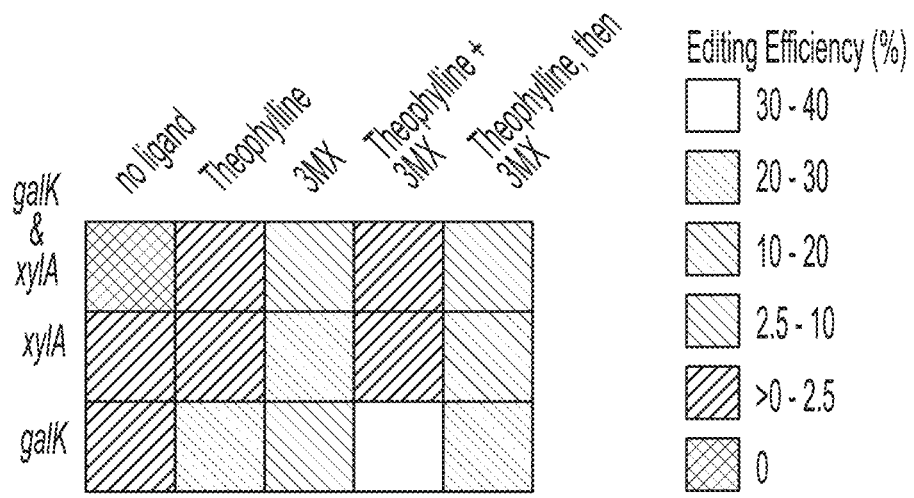
Figure 11:
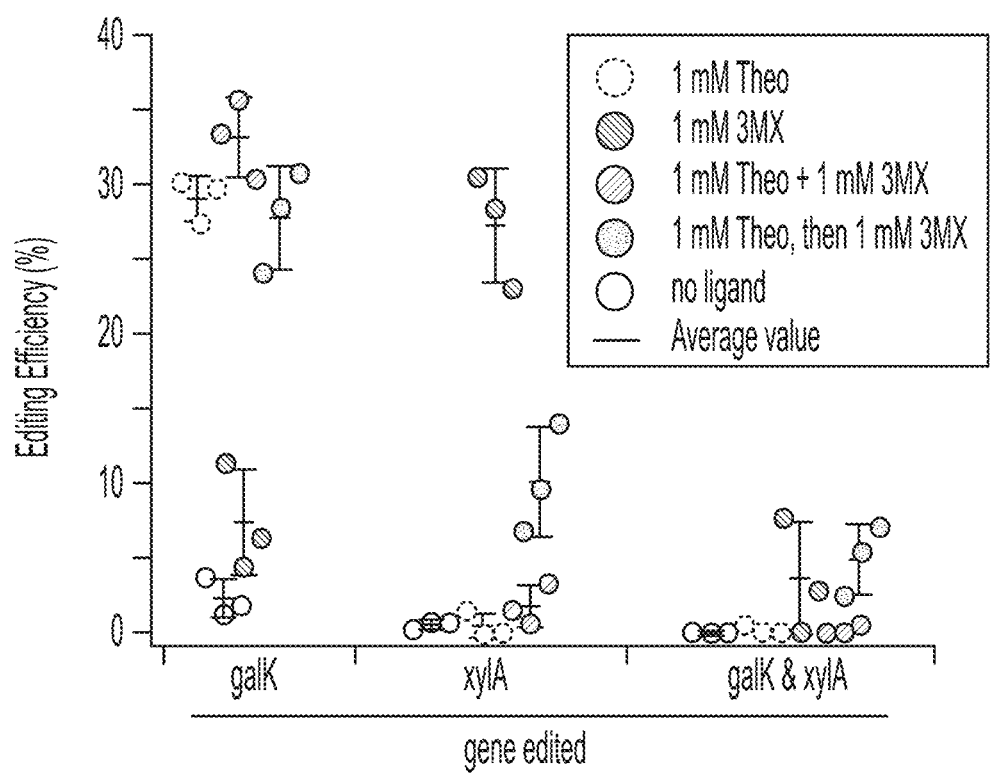
FIG. 11 is a graph which details the single data points summarized in FIG. 3D The underlying data is identical. Error bars indicate +/− standard deviation from the mean.

To further improve the utility of CRISPR-mediated recombineering, the agRNAs were applied to the problem of combinatorial edits. A hurdle impeding rapid throughput of combinatorial and multiple edits is that *E. coli* does not typically survive two simultaneous dsDNA breaks, even with induction of the λ-red proteins to facilitate homologous repair[10]. Therefore, only one mutation can be introduced in one round of CREATE editing. It was envisioned that the agRNAs would allow precise control over the timing of each editing event, facilitating the introduction of multiple designed edits into the same cell. A plasmid was designed that expressed a theophylline-regulated GU19-agRNA targeting galK1 and a 3-methylxanthine (3MX)-regulated A9-agRNA targeting the xylA gene. Furthermore, the plasmid also contained the homology arms necessary for repair and mutation of the respective cut sites (FIG. 3C). The plasmid construct was then used for a 3-hour induction with either 1 mM theophylline, 1 mM 3MX or a combination of the two and the transformed bacteria were plated on MacConkey agar that contained either galactose, xylose or both to assay editing of the galK and xylA genes with the red/white screen (FIG. 3D, FIG. 11). As expected, adding theophylline induced editing of the galK gene but not the xylA gene and adding 3MX induced mostly editing of xylA and to a lesser extent galK. This corresponds to previously described promiscuity of the theophylline aptamer[29]. Interestingly, a small number of transformants carried both mutations as a result. Simultaneously adding theophylline and 3MX led mostly to galK editing and few xylA edits. Adding first theophylline and after 3 hours adding 3MX for 2 hours led to an improved editing efficiency of xylA and resulted in transformants carrying both genomic edits. Thus, agRNAs can achieve CRISPR-mediated multiple genome editing in bacteria in a single step on a scale that allows the coverage of commonly used libraries.

In summary, an in vivo selection was developed which can be used to enrich ligand-activatable gRNAs. By stringently selecting for switchable agRNAs with low background activity, agRNAs that overcome the issue of leakiness associated with inducible promoters were obtained and allowed for a drastic improvement in the throughput of CRISPR-mediated recombineering by increasing the transformation efficiency $10^4$-fold and eliminating the bias for non-functional gRNAs. Furthermore, the combination of different guide-sequences with different aptamer-domains that bind distinct ligands allows orthogonal multiplexing of the agRNA activities enabling multiple, targeted mutations in a single experiment. The observation that many selected agRNAs could not recognize target sites other than the DNA target used in the selection might also show a way forward to reduce off-target cleavage in CRISPR applications.

TABLE 3

| Name | Sequence | Editing Efficiency no Theo | ±SD* | 1 mM Theo | ±SD* | SEQ ID NOs: |
|---|---|---|---|---|---|---|
| sgRNA | AGAGCTAGCAAGTT | 85%** | 1% | 89%** | 3% | 1 |
| Cassettes from initial Library | | | | | | |
| G1B1 | GTATCGCTTAAGCC | 1% | | 59% | | 2 |
| RG53 | AGTGAGCTAAAAAT | 0% | | 22% | | 3 |
| A38 | GAGAGGCCCCCGGC | 5% | | 85% | | 4 |
| A9 | TGAAGGCCGCAACA | 9%** | 7% | 81%** | 7% | 5 |
| A39 | AGAAGGCCCATCAT | 0% | | 7% | | 6 |
| A34 | TAGTTTAAACCGTT | 12% | | 57% | | 7 |
| A1 | GGGGGGCCTATTTT | 0% | | 66% | | 8 |
| A10 | GATGGGCCTCCACC | 0% | | 14% | | 9 |
| A14 | GGAGGTACGGTGCC | 2% | | 87% | | 10 |
| A19 | GAGAGGCCCCCGGC | 20% | | 90% | | 11 |

TABLE 3-continued

| Name | Sequence | Editing Efficiency no Theo | ±SD* | 1 mM Theo | ±SD* | SEQ ID NOs: |
|---|---|---|---|---|---|---|
| A8 | CGGGGGACAATAGG | 2% | | 82% | | 12 |
| A26 | GGGGGGCCACGCGC | 5% | | 89% | | 13 |
| C2A2 | TAGTGGCTACCATG | 5% | | 84% | | 14 |
| Cassettes from optimized libraries | | | | | | |
| AU1 | AGGGGGCCTATAAT | 0% | | 2% | | 15 |
| AU2 | ACCAGGCCAAGTAT | 0% | | 4% | | 16 |
| AU3 | ACAAGGCCCATAAT | 1% | | 72% | | 17 |
| AU4 | AACAGGCCTTAATT | 0% | | 0% | | 18 |
| AU5 | ACTCGGCCTGAACT | 0% | | 43% | | 19 |
| AU6 | AAGGGGCCTATAAT | 5% | | 77% | | 20 |
| AU7 | AGTAGGCCTTTCAT | 0% | | 58% | | 21 |
| AU8 | ACGGGGCCTAATAT | 0.3% | | 48% | | 22 |
| AU9 | AAACGGCCCACTGT | 1% | | 22% | | 23 |
| AU10 | ATAGGGCCATCCAT | 0% | | 13% | | 24 |
| AU11 | AATAGGCCACTTAT | 0% | | 25% | | 25 |
| AU12 | AGAGGGCCGGGCGT | 0% | | 26% | | 26 |
| AU14 | AGTGGGCCAGCCTT | 0% | | 17% | | 27 |
| AU15 | ACCCGGCCATTCAT | 0% | | 5% | | 28 |
| AU16 | AACCGGCCCCGAGT | 0% | | 6% | | 29 |
| AU17 | AAAGGGCCAGGCAT | 0% | | 4% | | 30 |
| AU18 | AATAGGCCCAGACT | 0% | | 7% | | 31 |
| AU19 | AATAGGCCCGCAGT | 0% | | 10% | | 32 |
| AU20 | AAATGGCCGGCAAT | 0% | | 0% | | 33 |
| GU1 | GACGGGCCTAATAT | 0% | | 0% | | 34 |
| GU2 | GCGAGGCCTACTAT | 0% | | 0% | | 35 |
| GU3 | GCAGGGCCTCATTT | 0% | | 0% | | 36 |
| GU4 | GATTGGCCATACAT | 0% | | 0% | | 37 |
| GU5 | GGTTGGCCTAATAT | 0% | | 2% | | 38 |
| GU6 | GGACGGCCAAGCAT | 0% | | 1% | | 39 |
| GU8 | GGCAGGCCTCTTCT | 0% | | 1% | | 40 |
| GU9 | GTTCGGCCCCGACT | 0% | | 0% | | 41 |
| GU10 | GTACGGCCCATAAT | 0% | | 0% | | 42 |
| GU11 | GTATGGCCTCGGAT | 0% | | 0% | | 43 |
| GU12 | GCCGGGCCTTTTTT | 0% | | 7% | | 44 |
| GU13 | GGCCGGCCAAGCAT | 0% | | 6% | | 45 |
| GU14 | GACTGGCCTATAAT | 0% | | 2% | | 46 |
| GU15 | GGACGGCCTACAAT | 0% | | 11% | | 47 |

TABLE 3-continued

| Name | Sequence | Editing Efficiency | | | | SEQ ID NOs: |
| --- | --- | --- | --- | --- | --- | --- |
| | | no Theo | ±SD* | 1 mM Theo | ±SD* | |
| GU16 | GGGAGGCCAGCGAT | 1% | | 0% | | 48 |
| GU17 | GTAAGGCCGCCGAT | 0% | | 0% | | 49 |
| GU18 | GATTGGCCTACGGT | 0% | | 1% | | 50 |
| GU19 | GATCGGCCATAGAT | 3%** | 3% | 64%** | 4% | 51 |
| GC1 | GCTGGGCCCTTCCC | 0% | | 0% | | 52 |
| GC2 | GTCAGGCCTATACC | 0% | | 0% | | 53 |
| GC3 | GTCCGGCCCCACAC | 0% | | 12% | | 54 |
| GC4 | GGTCGGCCAGTAGC | 0% | | 1% | | 55 |
| GC5 | GTTGGGCCGCGGAC | 0% | | 0% | | 56 |
| GC6 | GATTGGCCAGCAAC | 1% | | 40% | | 57 |
| GC7 | GGGGGGCCGAATAC | 1% | | 71% | | 58 |
| GC8 | GGACGGCCCTGTGC | 1% | | 0% | | 59 |
| GC9 | GCAGGGCCTCTAAC | 0% | | 0% | | 60 |
| GC10 | GAGCGGCCACAACC | 0% | | 0% | | 61 |
| GC11 | GCGTGGCCCTTCCC | 0% | | 3% | | 62 |
| GC12 | GATAGGCCAGTTAC | 1% | | 36% | | 63 |
| GC13 | GGAAGGCCTTATAC | 0% | | 64% | | 64 |
| GC15 | GCATGGCCTACTCC | 1% | | 21% | | 65 |
| GC16 | GATAGGCCAACACC | 1% | | 65% | | 66 |
| GC17 | GACCGGCCCCCCGC | 0% | | 2% | | 67 |
| GC18 | GATTGGCCGCAACC | 0% | | 48% | | 68 |
| GC20 | GCAAGGCCAACACC | 0% | | 64% | | 69 |

All sequence cassettes for the 2×4 IL and upper stem that were sequenced and tested are listed above with their respective editing efficiency at the galK 1 site when induced for 3 hours with 1 mM theophylline. For the avoidance of doubt, when expressed in a cell, the sequences in Table 3 would be RNA sequences, meaning that each T would be replaced with a U. *±SD represents the standard deviation from the mean. **The mean value was calculated from three biological replicates

TABLE 4

| Oligonucleotides | Sequence |
| --- | --- |
| theo_insert_B1 | GGTATAATACTAGTATGATAAAGCTGCTGCAATAGTTTTNNNNNNAT ACCAGCTTCGAAAGAAGCCCTTGGCAG (SEQ ID NO: 70) |
| theo_Insert_B2 | TTTTTCAAGTTGATAACGGACTAGCCTTATTTTNNNNNNNNCTGCCA AGGGCTTCTTTCGAAGCTG (SEQ ID NO: 71) |
| theo-gRNA_bbF | AAAACTATTGCAGCAGCTTTATCATACTAGTATTATACC (SEQ ID NO: 72) |
| theo-gRNA_bbR | AAAATAAGGCTAGTCCGTTATCAACTTGAAAAAG (SEQ ID NO: 73) |
| agRNA from Liu et al. | ATGATAAAGCTGCTGCAATAGTTTTAGAGCTAGAAATAGCAAGTTAA AATAAGGCTAGTCCGTTATCAACTTGAAAAAGTGGCACCGAGTCGGT |

TABLE 4-continued

| | |
|---|---|
| | GCCAGCAGCTTTATCATATACCACGCGAAAGCGCCTTGGCAGATGAT AAAGTTTTTTT (SEQ ID NO: 74) |
| CREATESeq_fwd | CTAAGGATGATTTCTGGAATTC (SEQ ID NO: 75) |
| CREATESeq_rev | CAGAACGCAGAAGCG (SEQ ID NO: 76) |
| guides of the gRNAs | Sequence |
| galK 1 | AUGAUAAAGCUGCUGCAAUA (SEQ ID NO: 77) |
| galK 2 | GAUCAGCGGCAAUGUGCCGC (SEQ ID NO: 78) |
| galK 3 | GUUCACCAAUCAAAUUCACG (SEQ ID NO: 79) |
| galK 4 | GACCGCGACUUCCAGUGAAG (SEQ ID NO: 80) |
| xylA | CAUAACGAACGCGAUCGAGC (SEQ ID NO: 81) |
| eGFP (non-targeting) | GACCAGGAUGGGCACCACCC (SEQ ID NO: 82) |
| mCherry | CCAAGCUGAAGGUGACCAA (SEQ ID NO: 83) |
| Homology Templates | Sequence |
| galK 1 | CCGCAGGGTGCCGGGTTAAGTTCTTCCGCTTCACTGGAAGTCGCGGT CGGAACGGTATTGCAGCAGCTTTAACATCTGCCGCTGGACGGCGCAC AAATCGCGCTTAACGGTCAGGAAGCA (SEQ ID NO: 84) |
| galK 2 | GAGCACCGCCTTCGTCTGTCGAGATAGGACATCTGCAACTGCGTAAC AACAGCTTCGGCGGCGTGGACATGGTGATCAGCGGCTAATAACCACA AGGTGCCGGGTTAAGTTCTTCCGCTTCACTGGAAGTCGCGGTCGGAA CCGTA (SEQ ID NO: 85) |
| galK 3 | GAGCACCGCCTTCGTCAGATCTGTAGTCCTCTGTTTGCCAACGCATT TGGCTACCCTGCCACTCACACCATTCAGGCGCCTGGCCGTGTTTAAT AAATTGGTGAACACACCGACTACAACGACGGTTTCGTTCTGCCCTGC GCGAT (SEQ ID NO: 86) |
| galK 4 | AAGAGCACCGCCTTCGTCGCTAAGTCTGACTCGGCGGCGTGGACATG GTGATCAGCGGCAATGTGCCGCAGGGTGCCGGGTTAAGTTCTTAATA AAGCCTGGAAGTCGCGGTCGGAACCGTATTGCAGCAGCTTTATCATC TGCCGC (SEQ ID NO: 87) |
| xylA | CATCACCCGCGGCATTACCTGATTATGGAGTTCAATATGCAAGCCTA TTTTGACCAATTAGACTAATAACGTTATGAAGGCTCAAAATCCTCAA ACCCGTTAGCATTCCGTCACTACA (SEQ ID NO: 88) |

DNA and RNA Sequences and oligonucleotides used in this study.

TABLE 5

| gRNA construct co-transformed with non-targeting gRNA | # of unedited colonies carrying non-targeting gRNA plasmid |
|---|---|
| A9 agRNA | 9/16 |
| GU19 agRNA | 6/16 |
| wt sgRNA | 16/16 |

The over-representation of plasmids expressing non-targeting gRNAs was confirmed by colony PCR and Sanger sequencing. 20 ng CREATE plasmids expressing a non-targeting gRNA were co-transformed with 180 ng of CREATE plasmid expressing a targeting gRNA construct and recovered with 1 mM theophylline. For each of those experiments, 16 colonies that showed up as unedited on the MacConkey agar were picked. For the experiments with A9 and GU19, the different sizes of the non-targeting wt sgRNA and the targeting agRNAs were used for differentiation via agarose gel electrophoresis after colony PCR. For the experiment with targeting and non-targeting wt sgRNA, Sanger sequencing was used to determine the identity of the transformed plasmid.

Materials and Methods

Strains and Plasmids

For molecular cloning, the E. coli strain E. Cloni® was used.

For the recombineering experiments, an E. coli MG1655 strain was used that contained two plasmids: The plasmid pSIM5, which expresses the λ-red proteins from a heat shock-inducible promoter and the X2-Cas9 plasmid (Addgene ID: 85811) that encodes Cas9 under control of the arabinose-inducible pBAD promoter. This strain will be referred to as MGλ9.

The gRNA constructs were constitutively expressed from a CREATE vector that was based on the pUC19 backbone. A CREATE vector also contains a template to introduce mutations at the genomic cut site during homologous repair[30].

Molecular Cloning

Homology-based cloning was used for construction of new plasmids. For generating plasmid backbones and inserts that contained homologous ends, PCR with the Q5® High-Fidelity 2× Master Mix was used. The annealing temperatures typically ranged from 60-72° C. For the cloning of single inserts, CPEC[31] was used. Libraries were constructed via Gibson Assembly using the NEBuilder® HiFi DNA Assembly Master Mix.

Library Design and Preparation

The double-stranded insert, containing the gRNA constructs, was generated by PCR assembly of two single-stranded oligos. A linearized vector backbone containing homology arms was produced by PCR from the galKOFF plasmid using the primers theo-gRNA_BBF and theo-gRNA_BBR. Insert and backbone were assembled by Gibson Assembly. The product was gel purified using a QIAquick Gel Extraction Kit and transformed into E. Cloni® bacteria via electroporation. The cells were recovered in SOB media for 1 hour and aliquots were plated on LB agar containing 100 µg/mL carbenicillin, which indicated that about $10^7$ CFU were recovered. The recovery culture was transferred to LB media containing 100 g/mL carbenicillin, grown for ~14 hours and then 150 µg plasmid library was harvested using a QIAprep Spin Miniprep Kit. Then, 0.5 µg of the plasmid library was electroporated into the MGλ9 strain 24 times to transform 12 µg DNA in total. The bacteria were recovered immediately in LB medium and aliquots were plated on LB agar after 1 hour to estimate the number of CFUs. Then, the MGλ9 culture was subjected to the galK selection assay. The 24 transformations yielded a total MGλ9 CFU of $3 \times 10^6$.

Cloning and Selection of the 14N Library

The first limiting step of the selection was the transformation of the cloning strain with the assembled plasmid library, which yielded about $10^7$ CFUs in total. The transformation of 12 g of this subset of the plasmid library into the MGλ9 strain was expected to yield a total number of CFUs of $6 \times 10^7$, based on control experiments with plasmids that express non-targeting gRNAs. Thus, the sub-library harvested from the E. Cloni® is expected to be transformed with 99.8% completion[20] into the MGλ9 strain. However, only $3 \times 10^6$ c.f.u.s were actually observed after transformation of MGλ9 with the subset of the plasmid library, which indicates that about 95% of the transformed plasmids probably expressed constitutively active agRNA constructs and the host cells transformed with these constructs were rapidly eliminated from the recovery culture due to cleavage of their genomic DNA.

GalK Selection Assay

Protocols from Warming et al.[33] were mostly followed, with the noticeable difference that the recombineering step was mediated by plasmids, using the CREATE technology, instead of using single-stranded oligos.

Negative selection: The library was transformed into MGλ9 cells without heatshock or addition of gRNA-ligand and recovered at 30° C. for 5 hours in LB containing 0.2% arabinose. The antibiotics chloramphenicol, kanamycin and carbenicillin were added 3 hours after transformation. Constitutively active gRNA constructs that allowed Cas9 activity in the absence of theophylline cause a double-stranded break, which leads to cell death.

Positive selection: The E. coli culture underwent recombineering as described in the section "CREATE Recombineering". However, after recovery the culture was not plated on MacConkey, but washed two times in M9 media to remove metabolizable sources of carbon and an aliquot was transferred to M63 selection media, which contained 0.2% glycerol, 0.2% 2-deoxygalactose, 1 mM $MgSO_4$ and kanamycin and carbenicillin, apart from the M63 salts. This media only permits growth of cells that introduced a stop codon into the galK gene. MG1655 cells typically plateau at a cell density of about $OD_{600}=2$ after 2-3 days in M63 media, so bacteria were added to an initial density of $OD_{600}<0.2$ to allow for enrichment of the editing cells via outgrowth. The cells were grown in the selection media at 37° C. for about 2-3 days or until an $OD_{600}$ of 1.5-2.0 was reached. Then, plasmids of the bacterial culture were harvested and the selection cycle can be repeated for further enrichment. After each transformation step, dilutions of the transformation culture were plated on LB agar to estimate the number of transformants.

Selection conditions were made increasingly stringent with increasing number of cycles by lowering the concentration of gRNA ligand progressively from 1 mM to 250 µM theophylline and by progressively shortening the time available for editing before transfer to selection media from 5 hours to 1 hour. In the third selection cycle, the positive selection was not carried out in liquid culture. Instead, the washed E. coli culture was plated on agar plates containing the M63 selection media. After incubating the plates at 37° C. for 2-3 days, colonies were picked from the M63 plates for screening.

CREATE Recombineering

Original Protocol:

The protocol established by Garst et al was mainly followed. LB containing kanamycin and chloramphenicol was inoculated with MGλ9 cells and grown overnight at 30° C. The stationary culture was diluted 100 fold in LB, containing chloramphenicol, kanamycin and 0.2% arabinose and grown to an $OD_{600}=0.4-0.6$ in 25 mL LB. The culture was heat-shocked in a shaking waterbath at 42° C. for 15 minutes to induce expression of the lambda-red proteins from pSIM5. Then, the culture was washed in two volumes of ice-cold deionized water, resuspended in 500 µl deionized water and 50 µl of the cell suspension was electroporated with 200 ng of a CREATE plasmid that encodes gRNA and homology template. The transformants were recovered in 4 mL of LB, containing 0.2% arabinose and optionally 1 mM theophylline or 1 µM anhydrotetracycline (ATC), and shaken at 37° C. for 3 hours before plating on MacConkey Agar. To estimate the number of cfu, aliquots were plated on LB agar 1 hour after transformation.

Aptamer-Protocol:

LB containing kanamycin and chloramphenicol was inoculated with MGλ9 cells and grown overnight at 30° C. The stationary culture was diluted 100 fold in LB, containing chloramphenicol and kanamycin and grown to an $OD_{600}=0.4-0.6$ in 25 mL LB. Then, the culture was washed in two volumes of ice-cold deionized water, resuspended in 500 µl deionized water and 50 µl of the cell suspension was electroporated with 200 ng of a CREATE plasmid that encodes gRNA and homology template. The transformants were recovered in 4 mL of LB, containing 0.2% arabinose and shaken at 30° C. for 1 hour. The culture was heat-shocked in a shaking waterbath at 42° C. for 15 minutes and 1 mM theophylline or 1 µM ATC was added to the culture. The culture was shaken at 37° C. for 3 hours before plating on MacConkey Agar. To estimate the number of cfu, aliquots were plated on LB agar 1 hour after transformation.

Multiplex-Protocol:

For the purpose of first adding theophylline and later 3MX to independently induce two different agRNAs, the protocol was slightly modified. First, the bacteria were prepared and transformed as in the original protocol, 1 mM theophylline was added to the media and the culture was shaken at 30° C. for three hours. Then, the culture was heat-shocked again at 42° C. for 15 minutes to induce expression of the lambda-red proteins again and 1 mM 3MX was added to the media. The culture was shaken at 37° C. for three hours and then plated.

Red/White Screening

In order to assess the frequency of gene editing, a red/white screen was used to visualize the introduction of a stop codon into the galK gene by CREATE. The original CREATE protocol was used for inducing gene editing and after 3 hours of recovery (with or without the agRNA ligand) a series of dilutions of the cultures were plated on MacConkey Agar plates containing 1% galactose. Bacterial colonies with a mutated galK* site appear white on the plates, whereas non-edited colonies appear red. The editing efficiency could be calculated by dividing the number of edited colonies over the total number of colonies. By comparing the editing efficiency in presence versus absence of the ligand, a dynamic range of the in vivo activity could be determined.

When screening the enriched libraries for switchable constructs, the transformants were recovered in 4 mL of LB broth, a dilution series was plated for every construct and the experiment was only carried out once due to the large volume of colonies screened (~250 in total). When the constructs A9 and GU19 were characterized in detail, triplica of the experiment were carried out. This may account for differences in the observed editing efficiency from the initial screen (FIG. 6) and the values from FIG. 2A.

Calculation of Plasmid Enrichment

When the *E. coli* strain MGλ9 is transformed exclusively with the CREATE galKOFF plasmid that expresses wt sgRNA that targets the galK gene, 100% of the transformants carry the targeting plasmid and 88.9% of the bacterial population is edited after the CREATE procedure. When transforming a mixture of targeting plasmid and non-targeting plasmid in a 9:1 ratio, 80% of the bacteria are expected to be edited according to 0.9×88.9%=80.1%, assuming no bias for the non-targeting plasmid. However, only 13.5% of the plated colonies were edited, which means that 15.2% of plated bacteria are expected to carry the targeting CREATE plasmid, when considering that only 88.9% of bacteria that are transformed with the targeting plasmid get edited:

$$\frac{13.5\%}{88.9\%} = 15.2\%.$$

This means, that 100−15.2=84.8% of the plated bacteria carry the 88.9% non-targeting plasmid, which is a ~8.5-fold enrichment over the 10% of non-targeting plasmid in the transformation mix.

A formalized description would be:
- $P_{Nt}$=Fraction of plasmids with non-targeting gRNA
- $E_t$=Editing efficiency of the targeting gRNA
- $E_{nt}$=Editing efficiency obtained from mix with non-targeting plasmids as observed
- $T_t$=Fraction of transformants with the targeting gRNA plasmid
- $T_{nt}$=Fraction of transformants with non-targeting gRNA plasmid $$\text{Enrichment of non-targeting } gRNA \text{ plasmid} = \frac{T_{nt}}{P_{nt}} = \frac{1-T_t}{P_{nt}} = \frac{1-\left(\frac{E_{nt}}{E_t}\right)}{P_{nt}}$$

The error is given as ±standard deviation.

Cas9 Expression and Purification

*Streptococcus pyogenes* Cas9 (pMJ915) construct was a gift from Jennifer Doudna (Addgene plasmid #69090)[34]. The construct was transformed into BL21 (DE3) Rosetta *Escherichia Coli* cells. 10 mL LB-Ampicillin bacterial culture was grown overnight and then inoculated into 1 L LB medium. Culture was incubated at 37° C. until $OD_{600nm}$ reached around 0.6. The culture was cooled down to approximately 20° C. in a cold water bath and protein expression was induced by adding 0.5 mM Isopropyl b-D-1-thiogalactopyronoside (IPTG). The culture was grown in a 20° C. shaker overnight. Bacterial cells were pelleted at 1,500 g and resuspended in lysis buffer (1 M KCl, 20 mM HEPES pH 7.5, 20% glycerol, 1 mM TCEP, 10 mM Imidazole). Cells were lysed using an Emulsiflex C3 homogenizer. The cell lysates were clarified by centrifugation at 17,000 g for 30 minutes. Polyethyleneimine (PEI) was used to precipitate the nucleic acid contaminants[35]. The supernatant (35 mL) was put into a beaker 4° C. and 250 µL 5% PEI was slowly added during stirring. The supernatant was stirred for 15 more minutes. Then, it was centrifuged at 12,000 g for 20 minutes to pellet the nucleic acid contaminants. The supernatant was taken and its PEI concentration was brought to 0.1% and stirred at 4° C. for 15 minutes. It was centrifuged at 12,000 g for 20 minutes. Then, the supernatant was incubated with Ni-NTA sepharose beads on an orbital shaker for 1 hour at 4° C. Beads were centrifuged at 300 g for 2 minutes and washed 3 times in lysis buffer and once in lysis buffer supplemented with 100 mM Imidazole. Proteins were eluted in lysis buffer supplemented with 250 mM Imidazole. The eluate was concentrated and the buffer was exchanged (20 mM HEPES pH 7.5, 500 mM KCl, 1 mM TCEP, 10% glycerol). Then, size exclusion purification was conducted on a Hiload 16/600 Superdex 200 column (AKTA Purifier system (GE Healthcare)). Cas9 protein was purified as monomer, based on comparison to size standards. Final protein concentration was calculated using molar extinction coefficient as determined using the Expasy-Protparam tool and the absorbance at 280 nm. Cas9 was kept at −20° C.

In Vitro Transcription and Purification of gRNAs

DNA template for RNA transcription was amplified by using PCR and transcribed by T7 RNA polymerase. For a 3 mL transcription reaction, 1.9 mL ddH₂O, 0.3 mL transcription buffer (10×), 100 µl MgCl₂ (1 M), 125 µl from each rNTPs (100 mM), 200 µl PCR template, 31 µl DTT (1 M), 25 µl inorganic pyrophosphatase (20 U/µl), 50 µl T7 RNA polymerase were assembled in a 15 mL canonical. The reaction was vortexed and incubated at 37° C. for 2 hours. Then, 6 mL ethanol was added to the reaction and kept at −80° C. for at least 30 minutes or at 20° C. for overnight to precipitate the RNA. The tubes are centrifuged at 4,000 g and at 4° C. for 15 minutes. The supernatant was discarded and pellet was left for air-drying to evaporate the ethanol at room temperature. The pellet was suspended in 2 mL of 8 M urea, 500 µL 0.5 M EDTA pH 8.0, and 1 mL of formamide loading dye. To re-suspend all of the precipitate the tube was vortexed vigorously. To ensure the complete denaturation of the RNA, samples were heated at 65° C. for 5 minutes and vortexed vigorously until getting a clear solution. Transcripts were purified using denaturing polyacrylamide gel (6-10% 29:1 acrylamide/bisacrylamide, 1×TBE buffer (0.1 M Tris base, 0.8M boric acid, 1 mM Na₂EDTA), 8 M urea). RNA bands were visualized by putting the gel on a fluorescence TLC plate and shadowing the RNA with short-wave UV in a dark room. Full-length transcripts were excised from the gel and the gel pieces were further crushed into small pieces inside a tube. 0.5×TE buffer was added to the tube and the mix was shaken gently at 4° C. for 2 hours to extract the RNA. RNA from the supernatant was concentrated using centrifugal concentrators with a 10 kDa molecular weight cutoff (Amicon Ultra, 0.5 mL) and buffer (0.5× TE) exchange was performed by the same method. Final RNA concentration was calculated using the absorbance at 260 nm and the molar extinction coefficient as determined using an extinction coefficient calculator that calculates the extinction coefficients by summing of the individual extinction coefficients for each nucleotide in the RNA. The RNA was aliquoted into 5 µl volumes and stored at −20° C. until use.

Body Radiolabeling Reaction of gRNAs

100 µl in vitro RNA transcription reaction was prepared with an adenine ribonucleotide concentration that is 10-fold lower than the standard reaction concentration. 20 µCi ATP [α-32P] was added and the reaction was carried out with T7 RNA polymerase at 37° C. for 2 hours. MicroSpin G25 columns were used to remove unincorporated nucleotides from the labeling reactions. Radiolabeled transcripts were purified using 6% denaturing polyacrylamide gel (29:1 acrylamide/bisacrylamide, 1×TBE buffer, 8 M urea). The gel was exposed using a phosphoimager for about 10-15 minutes and the screen was imaged by using a Typhoon PhosphoImager. The image was printed out with actual sizes. The gel was placed on top of the printed image and the corresponding RNA band was excised from the gel. Gel pieces were put into 2 mL eppendorf tubes and crushed into small pieces by using 1 mL pipette tip. 0.5×TE buffer with 0.3 M sodium acetate (pH 5.3) was added into the tube and left for elution by rotating at 4° C. for 2 hours. The radiolabeled RNAs were precipitated with ethanol and glycogen at −80° C. for 30 minutes (or overnight at −20° C.) and centrifuged at 17,000 g for 30 minutes at 4° C. Precipitated RNA was resuspended in 0.5×TE buffer and quantified by liquid scintillation counting.

Electrophoretic Mobility Shift Assay (EMSA)

EMSA experiments were carried out to measure dissociation constants (Kd) of the Cas9 binding to gRNAs (FIG. 10) reactions. gRNAs were radiolabeled as described above. They were heated at 95° C. for 3 minutes and snap cooled before addition to the binding reactions. Cas9 proteins (0-5 nM) were incubated with trace amount of (~0.05 nM) radiolabeled RNA molecules in binding buffer containing 20 mM HEPES pH 7.5, 200 mM KCl, 5 mM DTT, 5% glycerol, 0.01% NP40 with or without 250 µM theophylline. A native polyacrylamide (6%, 29:1 acrylamide/bisacrylamide) supplemented with 0.5×TB (45 mM Tris-HCl, 45 mM borate, pH 8.1) buffer was used to separate the bound and unbound gRNA species. Gels were dried and subsequently imaged using a Typhoon PhosphoImager (Molecular Dynamics) and the signals were quantified with ImageQuant software suite. Quantified data was fit to a standard two-state binding isotherm using Igor (Wavemetrics), allowing calculation of both dissociation constants and Hill Coefficients.

What is claimed is:

1. A guide RNA (sgRNA) comprising a small-molecule-binding aptamer sequence adjacent to a region comprising a 2×4 internal loop and a region comprising an upper stem, wherein the small-molecule-binding aptamer is a theophylline-binding aptamer and the theophylline-binding aptamer comprises at least 85% homology to a polynucleotide represented by the sequence 5'-AUACCAGCUUCGAAAGAAGCCCUUGGCAG-3' (SEQ ID NO: 95).

2. The sgRNA of claim 1, wherein sgRNA comprises up to 2 nucleotides between the small-molecule-binding aptamer sequence and the 2×4 internal loop.

3. A ribonucleoprotein (RNP) comprising an sgRNA of claim 1 and a Cas enzyme.

4. The RNP of claim 3, wherein the Cas enzyme is Cas9.

5. The RNP of claim 3, wherein the region comprising the 2×4 internal loop and the region comprising the upper stem comprises the sequence of SEQ ID NO: 169.

6. The RNP of claim 3, wherein the region comprising the 2×4 internal loop and the region comprising the upper stem comprises the sequence of SEQ ID NO: 100.

7. A method of inducing gene editing in a bacterium, the method comprising:
 a. introducing or expressing the sgRNA of claim 1 in a bacterium,
 b. introducing or expressing a Cas enzyme in the bacterium, and
 c. contacting the bacterium with a small molecule that interacts with the small-molecule-binding aptamer sequence in the sgRNA such that gene editing is induced in the bacterium.

8. The method of claim 7, wherein the Cas enzyme is Cas9.

9. The method of claim 7, wherein the sgRNA exhibits greater than or equal to 10-fold induction in editing in presence of a small molecule ligand that binds to the small-molecule-binding aptamer sequence.

10. An in vivo method of selecting in bacteria a switchable aptamer single guide RNA (agRNA) that is inducible with a small molecule, wherein the switchable agRNA comprises a single guide RNA of claim 1, the method comprising:
 a. performing a negative selection step comprising growing a first plurality of bacteria in absence of the small molecule and in the absence of X-red protein expression, inducing cell death in a subset of the plurality of bacteria to produce a second plurality of bacteria, wherein individual bacteria in the first plurality of bacteria comprise a nucleic acid encoding the candidate agRNA comprising the sgRNA of claim 1 that produces a cut site in a gene encoding a selection marker protein; a Cas enzyme; and a template for homologous repair of the cut site in the gene encoding the selection marker protein;
 b. performing a positive selection step comprising either:
 i. growing the second plurality of bacteria in the presence of the small molecule and red protein expression; or
 ii. isolating nucleic acids encoding the candidate agRNAs comprising the sgRNA of claim 1 from the second plurality of bacteria and introducing the nucleic acids into a third plurality of bacteria and growing the third plurality of bacteria in the presence of the small molecule and X-red protein expression, wherein individual bacteria in the third plurality comprise a nucleic acid encoding a candidate agRNA that produces a cut site in the gene encoding a selection marker protein, a Cas enzyme, and a template for homologous repair of the cut site in the gene that encodes the selection marker protein; and
 c. selecting at least one bacterium from b. that expresses an altered selection marker protein.

11. The method of claim 10, wherein the selection marker protein is galK and the template for homologous repair comprises a premature stop codon for a galK gene.

12. An in vivo method of selecting in bacteria a switchable aptamer single guide RNA (agRNA) that is inducible with a small molecule, wherein the switchable agRNA comprises a single guide RNA of claim 1, the method comprising:
 a. performing a negative selection step comprising growing a first plurality of bacteria in absence of the small molecule and in presence of X-red protein expression and inducing cell death in a subset of a first plurality of bacteria to produce a second plurality of bacteria, wherein individual bacteria in the first plurality of bacteria comprise a nucleic acid encoding the candidate agRNA comprising the sgRNA of claim 1 that produces a cut site in a gene encoding a selection marker protein, a Cas enzyme, and a template for homologous repair of the cut site in the gene that encodes the selection marker protein;
 b. performing a positive selection step comprising either:
 i. growing the second plurality of bacteria in the presence of the small molecule and X-red protein expression; or
 ii. isolating nucleic acids encoding candidate agRNAs from the second plurality of bacteria and introducing the nucleic acids into a third plurality of bacteria and growing the third plurality of bacteria in the presence of the small molecule and λ-red protein expression, wherein individual bacteria in the third plurality comprise a nucleic acid encoding the candidate agRNAs comprising the sgRNA of claim 1 that produces a cut site in the gene encoding a selection marker protein, a Cas enzyme, and a template for homologous repair of the cut site in the gene that encodes the selection marker protein; and
 c. selecting at least one bacterium from b. that expresses the selection marker protein.

13. The sgRNA of claim 1, wherein the region comprising the 2×4 internal loop and the upper stem comprises the sequence of SEQ ID NO: 169.

14. A composition comprising: (i) the sgRNA of claim 1; or (ii) a vector expressing the sgRNA of claim 1.

15. The sgRNA of claim 1, wherein the small-molecule-binding aptamer is a theophylline-binding aptamer, and the theophylline-binding aptamer comprises the polynucleotide represented by the sequence 5'-AUACCAGCUUCGAAAGAAGCCCUUGGCAG-3' (SEQ ID NO: 95).

16. A guide RNA (sgRNA) comprising a small-molecule-binding aptamer sequence adjacent to a region comprising a 2×4 internal loop and a region comprising an upper stem, wherein the region comprising the 2×4 internal loop and the upper stem comprises the sequence 5'-GNNNGGAUACCAGCUUCGAAAGAAGCCNUUGGCAGCCNNNNNC-3' (SEQ ID NO: 169).

17. The sgRNA of claim 16, wherein sgRNA comprises up to 2 nucleotides between the small-molecule-binding aptamer sequence and the 2×4 internal loop.

18. A guide RNA (sgRNA) comprising a small-molecule-binding aptamer sequence adjacent to a region comprising a 2×4 internal loop and a region comprising an upper stem, wherein the region comprising the 2×4 internal loop and the upper stem comprises a polynucleotide represented by SEQ

ID NO: 100, UGAAGGAUACCAGCUUCGAAAGAAGCCNUUGGCAGCCGCAACA.

19. The sgRNA of claim 18, wherein sgRNA comprises up to 2 nucleotides between the small-molecule-binding aptamer sequence and the 2×4 internal loop.

* * * * *

UNITED STATES PATENT AND TRADEMARK OFFICE
CERTIFICATE OF CORRECTION

PATENT NO. : 12,416,008 B2  
APPLICATION NO. : 17/375808  
DATED : September 16, 2025  
INVENTOR(S) : Robert Batey et al.

Page 1 of 1

It is certified that error appears in the above-identified patent and that said Letters Patent is hereby corrected as shown below:

In the Claims

- In Claim 10, Column 111, Line 46, replace "X-red" with "λ-red" prior to 'protein'.

- In Claim 10, Column 111, Line 58, insert --λ- -- prior to 'red'.

- In Claim 10, Column 111, Line 64, replace "X-red" with "λ-red" prior to 'protein'.

- In Claim 12, Column 112, Line 16, replace "X-red" with "λ-red" prior to 'protein'.

- In Claim 12, Column 112, Line 28, replace "X-red" with "λ-red" prior to 'protein'.

Signed and Sealed this  
Ninth Day of December, 2025

John A. Squires  
*Director of the United States Patent and Trademark Office*